US005691181A

United States Patent [19]
Lowe

[11] Patent Number: 5,691,181
[45] Date of Patent: Nov. 25, 1997

[54] DNA ENCODING LIPASE FROM HUMAN GASTRIC MUCOSAL TISSUE

[75] Inventor: Peter Anthony Lowe, Reading, United Kingdom

[73] Assignee: Celltech Limited, Berkshire, United Kingdom

[21] Appl. No.: 340,123

[22] Filed: Nov. 15, 1994

Related U.S. Application Data

[62] Division of Ser. No. 97,619, Jul. 27, 1993, abandoned, which is a continuation of Ser. No. 996,488, Dec. 28, 1992, abandoned, which is a continuation of Ser. No. 750,704, Aug. 20, 1991, abandoned, which is a continuation of Ser. No. 554,062, Jun. 26, 1990, abandoned, which is a continuation of Ser. No. 865,564, Apr. 21, 1986, abandoned.

[30] Foreign Application Priority Data

Aug. 21, 1984 [GB] United Kingdom ............ 8421210

[51] Int. Cl.$^6$ ............... C12N 9/20; C12N 15/55; C12N 15/85
[52] U.S. Cl. .......... 435/240.1; 435/198; 435/320.1; 435/252.3; 435/240.2; 536/23.2; 536/23.4
[58] Field of Search .............. 435/198, 69.7, 435/69.8, 320.1, 252.3, 240.1, 2, 240.4; 536/23.2, 23.4

[56] References Cited

U.S. PATENT DOCUMENTS

| | | | |
|---|---|---|---|
| 3,493,652 | 2/1970 | Hartman | 424/94.63 |
| 4,013,784 | 3/1977 | Speiser | 424/19 |
| 4,202,824 | 5/1980 | Umezawa et al. | 260/343.9 |
| 4,338,397 | 7/1982 | Gilbert et al. | 435/68 |
| 4,411,994 | 10/1983 | Gilbert et al. | 435/69.7 |
| 4,703,004 | 10/1987 | Hopp et al. | 435/69.7 |
| 4,738,921 | 4/1988 | Belagaji et al. | 435/69.7 |
| 4,745,055 | 5/1988 | Schenk et al. | 435/69.7 |
| 4,755,383 | 7/1988 | Fujii et al. | 424/94.63 |
| 4,769,326 | 9/1988 | Rutter | 435/69.7 |

FOREIGN PATENT DOCUMENTS 2091268  7/1982  United Kingdom .

OTHER PUBLICATIONS

Schonheyder et al., "The Gastric Lepase in Man", *Acta Physiol Scans*, vol. 11, pp. 349–389, 1946.

Perret et al., "Gastric Lipolysis in the Young Rabbit.Origins and Physiclogical Importance of Lipase", *Chemical Abstracts* vol. 97 No. 124832v, 1982.

Tiruppathi, C. et al., "Purification and Properties of an Acid Lipase from Gastric Juice", *Biochim et Biophys. Acta* 712; pp. 692–697 (1982).

Young, R.A. et al., "Efficient Isolation of Genes of Using Antibody Probes", *Proc. Natl. Acad. Sci.* 80; pp. 1194–1198 (1983).

Suggs, S.V. et al., "Use of Synthetic Oligonucleotides as Hybridization Probes: Isolation of Cloned cDNA Sequences for Human B2-Microglobulin", *Proc. Natl. Acad Sci.* 78; pp. 6613–6617 (1981).

Bernbäck, S. et al; Purification and Molecular Characterization of Bovine Pregastric Lipase; Eur J. Biochem 148 (2) pp. 233–238 (1985).

Tiruppathi, C. et al; Purification and Properties of an Acid Lipase from Gastric Juice; Biochim et Biophys Acta 712 pp. 692–697 (1982).

Moreau et al., "Screening of Preduodenal Lipases in Several Mammals", Biochimica Biophysica Acta, 959, 247–252, 1988.

Bernback et al, Purification and molecular characterization of bovine pregastric lipase; Eur. J. Biochem, 148(2), pp. 233–238 (1985).

Tirruppathi et al, Purification and properties of an acid lipase from gastric juice, Biochim and Biophys Acta, 712, pp. 692–697 (1982).

Chemical Abstracts, vol. 71, No. 23, Dec. 8, 1969, "Purification from porcine pancrease of two molecular species of with lipase activity", No. 109248d.

Chemical Abstracts, vol. 96, No. 11, Mar. 15, 1982, "Porcine pancreatic lipase. Completion of the primary structure", No. 81865t.

Chemical Abstracts, vol. 96, No. 7, Feb. 15, 1982, "Comparative studies of human and porcine pancreatic lipases" N–terminal sequence sulfhydryl groups and interfacial activity; No. 48236r.

Chemical Abstracts, vol. 97, No. 21, Nov. 22, 1982, "Purification and properties of an acid lipase from human gastric juice", No. 177584x.

Chemical Abstracts, vol. 97, No. 25, Dec. 20, 1982, "Cloning of a phosphate–regulation hemolysin gene (phospholipase C) from *Pseudomonas aeruginosa*", No. 209601u.

Siurala, M. Lipase Activity of the Gastric Mucose of Man Under Pathological Conditions, Dept. of Pathology, University of Helsinki, Methods and Material, pp. 268–279, 1956.

Cohen et al., Lipolytic Activity of Human Gastric and Duodenal Juice Against Medium and Long Chain Triglycerides, Gastroenterology, 1971:60, 1–15.

Szafran et al., Electropheretic Properties and Specify of Human Gastric Lipase, Enzyme 23: 187–193, 1978.

Szafran et al., Coupled Secretion of Gastric Lipase and Pepsin in Man following Pentagastrin Stimulation, Digestion 18: 310–318 (1978).

(List continued on next page.)

*Primary Examiner*—Robert A. Wax
*Assistant Examiner*—Keith D. Hendricks
*Attorney, Agent, or Firm*—Spencer & Frank

[57] ABSTRACT

A human gastric lipase protein for use in the treatment of lipase deficiency. A process is described for producing gastric lipase using recombinant DNA technology to produce a host organism (for example *E. coli*) capable of producing a methionine-gastric lipase or precursor of the gastric lipase which may be cleaved to yield the gastric lipase. The host organism is transformed with a vector including a gene coding for a methionine-gastric lipase or a precursor of gastric lipase. The precursor protein is for example, pregastric lipase protein, or a fusion protein comprising gastric lipase and a heterologous protein. A pharmaceutical composition in unit dosage or liquid form is described.

22 Claims, 13 Drawing Sheets

OTHER PUBLICATIONS

Szafran et al., Sequential Hydrolysis of Three Acyl Ester Bonds in Triolein Molecule by Human Gastric Juice Lipase, Enzyme 30: 115–121, (1983).

Hamosh, Lipases, 1984, Ed Borgstrom, Elsevier, pp. 50–81.

Bodmer et al., Molecular Cloning of a Human Gastric Lipase and Expression of the Enzyme in Yeast, Biochimica et Biophysica Acta 909 (1987) 327–244.

DeNigris et al., Secretion of Human Gastric Lipase From Dispersed Gastric Glands, Biochimica et Biophysica Acta 836, (1985) 67–72.

Abrams et al., Gastric Lipase: Localization in the Human Stomach, Gastroenterology, 1988:95, 1460–1464.

Gagouri et al., Kinetic Assay of Human Gastric Lipase on Short and Long Chain Triacylglycerol Emulsions, Enzymes of Lipid Metabolism, vol. 116, pp. 19–22, Plenum Press, 1986.

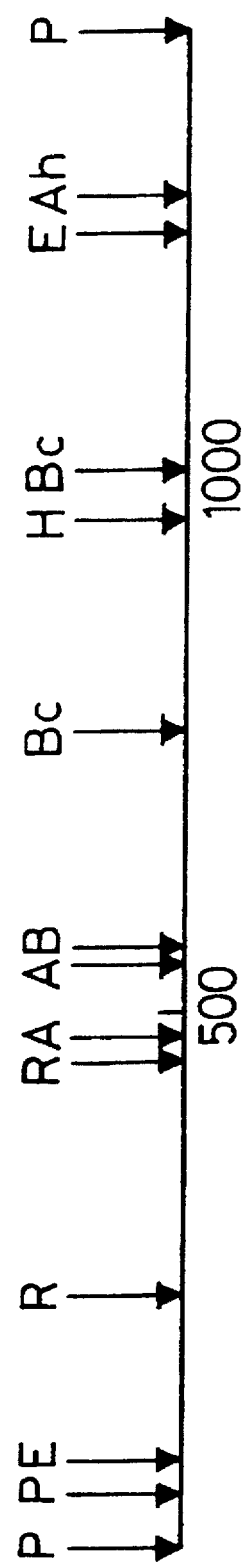
FIG. 2(a)
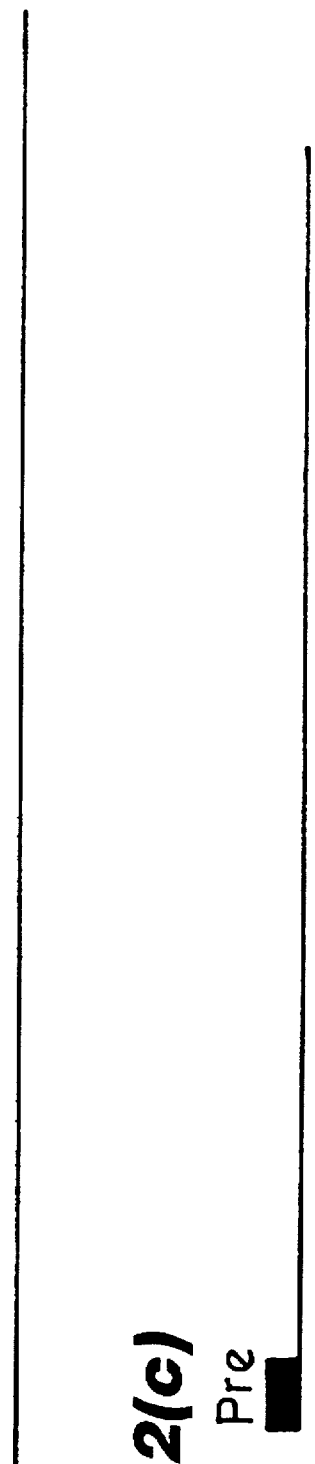
FIG. 2(b)
FIG. 2(c)

```
                                                                      M  W  L  L  L
AGAGAAACAGAATCCTAACTATTTCTGAGGAAACTGCAGGTCCAAAATGTGGCTGCTTTT
         10           20          30           40         50        60

P  I  S  P  E  V  T  M  I  I  S  Q  M  I  T  Y  W  I  Y  P
 P     G  S  P  E  V  T  M  N  I  S  Q  M  T  Y  W  G  Y
TCCTGGAAGCCCCTGAAGTGACTATGAACATTAGTCAGATGATTACTTATTGGGGATACCC
         130          140         150          160         170       180

Y  G  K  K  N  S  G  N  T  G  Q  R  P  V  V  F  L  Q  H  G
TTATGGGAAGAAAAATTCAGGGAATACAGGCCAGAGACCTGTTGTGTTTTGCAGCATGG
         250          260         270          280         290       300
                                           100

L  A  D  A  G  Y  D  V  W  L  G  N  S  R  G  N  T  W  A  R
TCTGGCAGATGCTGGTTATGATGTGTGGCTGGGCAACAGCAGAGGAAACACCTGGGCCAG
         370          380         390          400         410       420

A  K  Y  D  L  P  A  T  I  D  F  I  V  K  K  T  G  Q  K  Q
GGCTAAATATGACCTTCCAGCCACAATCGACTTCATTGTAAAGAAAACTGGACAGAAGCA
         490          500         510          520         530       540

P  S  L  A  K  R  I  K  T  F  Y  A  L  A  P  V  A  T  V  K
TCCCAGCCTGGCTAAAAGAATCAAAACCTTCTATGCTCTAGCTCCTGTTGCCACTGTGAA
         610          620         630          640         650       660
```

```
         T   M   A   S   L   I   S   V   L   G   T   T   H   G  -1 +1 L   F   G   K   L   H
        AACAATGGCAAGTTTGATATCTGTACTGGGGACTACACACATGG TTGTTTGGAAAATTACA
                70          80          90          100    L   F   G   K   L
                                                            110         120

N     N   E   E   Y   E   V   T   E   D   G   Y   I   L   E   V   N   R   I   P
        AAATGAAGAATATGAAGTTGTGACTGAAGATGGTTATATTCTTGAAGTCAATAGAATTCC
                190         200         210         220         230         240

L   L   A   S   A   T   N   W   I   S   N   L   F   N   N   S   L   A   F   I
        TTTGCTTGCATCAGCCACAAACTGGATTTCCAACCTGCCGAACAACAGCCTTGCCTTCAT
                310         320         330         340         350         360

R   N   L   Y   S   P   D   S   V   E   F   W   A   F   S   F   D   E   M
        AAGAAACTTGTACTATTCACCAGATTCAGTTGAATTCTGGGCTTTCAGCTTTGATGAAAT
                430         440         450         460         470         480

L   H   Y   V   G   H   S   Q   G   T   T   I   G   F   I   A   F   S   T   N
        GCTACACTATGTTGGCCATTCCCAGGGCACCACCATTGGTTTTATTGCCTTTTCCACCAA
                550         560         570         580         590         600
                                        200

Y   T   K   S   L   I   N   K   L   R   F   V   P   Q   S   L   F   K   F   I
        GTATACAAAAAGCCCTTATAAAACAAACTTAGATTTGTTCCTCAATCCCTCTTCAAGTTTAT
                670         680         690         700         710         720
```

```
      F   G   D   K   I   F   Y   P   H   N   F   F   D   Q   F   L   A   T   E   V
     ATTTGGTGACAAAATATTCTACCCACACAACTTCTTTGATCAATTTCTTGCTACTGAAGT
        730         740         750         760         770         780

D   S   K   N   F   N   I   S   R   L   D   V   Y   L   S   H   N   P   A   G
     TGACAGTAAGAACTTTAACACGAGTCGCTTGGATGTGTATCTATCACATAATCCAGCAGG
        850         860         870         880         890         900
                                                                          300

Y   D   W   G   S   P   V   Q   N   R   M   H   Y   D   Q   S   P   P   Y
     TTATGACTGGGGAAGCCCAGTTCAGAATAGGATGCACTATGATCAGTCCCCAACCTCCCTA
        970         980         990        1000        1010        1020

A   D   P   Q   D   V   G   L   L   L   P   K   L   P   N   L   I   Y   H   K
     GGCTGACCCCCAAGATGTTGTTGGCCTTTTGCTTCCAAAACTCCCCAATCTTATTTACCACAA
       1090        1100        1110        1120        1130        1140

Y   N   D   I   V   S   M   I   S   E   D   K   K   *
     TTACAATGACATTGTTTCTATGATATCAGAAGATAAAAAGTAGTTCTGGATTTAAAGAAT
       1210        1220        1230        1240        1250        1260
                              379

ACATGCAGTGCTTCTTTCTGTAATTTTTGACTTTAGAAATATATTGGC
       1330        1340        1350        1360          1
```

FIG. 3(c)

```
      C  S  R  E  M  L  N  L  L  C  S  N  A  L  F  I  I  C  G  F
     GTGCTCCCGTGAGATGCTGAATCTCCTTTGCAGCAATGCCTTATTATAATTTGTGGATT
              790       800       810       820       830       840

T  S  V  Q  N  M  F  H  W  T  Q  A  V  K  S  G  K  F  Q  A
     AACTTCTGTTCAAAACATGTTCCATTGGACCCAGGCTGTTAAGTCTGGGAAATTCCAAGC
              910       920       930       940       950       960
                                              350
      Y  N  V  T  A  M  N  V  P  I  A  V  W  N  G  G  K  D  L  L
     CTACAATGTGACAGCCATGAATGTACCAATTGCAGTGTGGAACGGGTGGCAAGGACCTGTT
             1030      1040      1050      1060      1070      1080

E  I  P  F  Y  N  H  L  D  F  I  W  A  M  D  A  P  Q  E  V
     GGAGATTCCTTTTTACAATCACTTGGACTTTATCTGGGCAATGGATGCCCCTCAAGAAGT
             1150      1160      1170      1180      1190      1200

TATCCGTTTGTTTTTCCAAAAATACTTTTATTCTTCTCATACATAGTATTTTCATAATGTTTG
             1270      1280      1290      1300      1310      1320
```

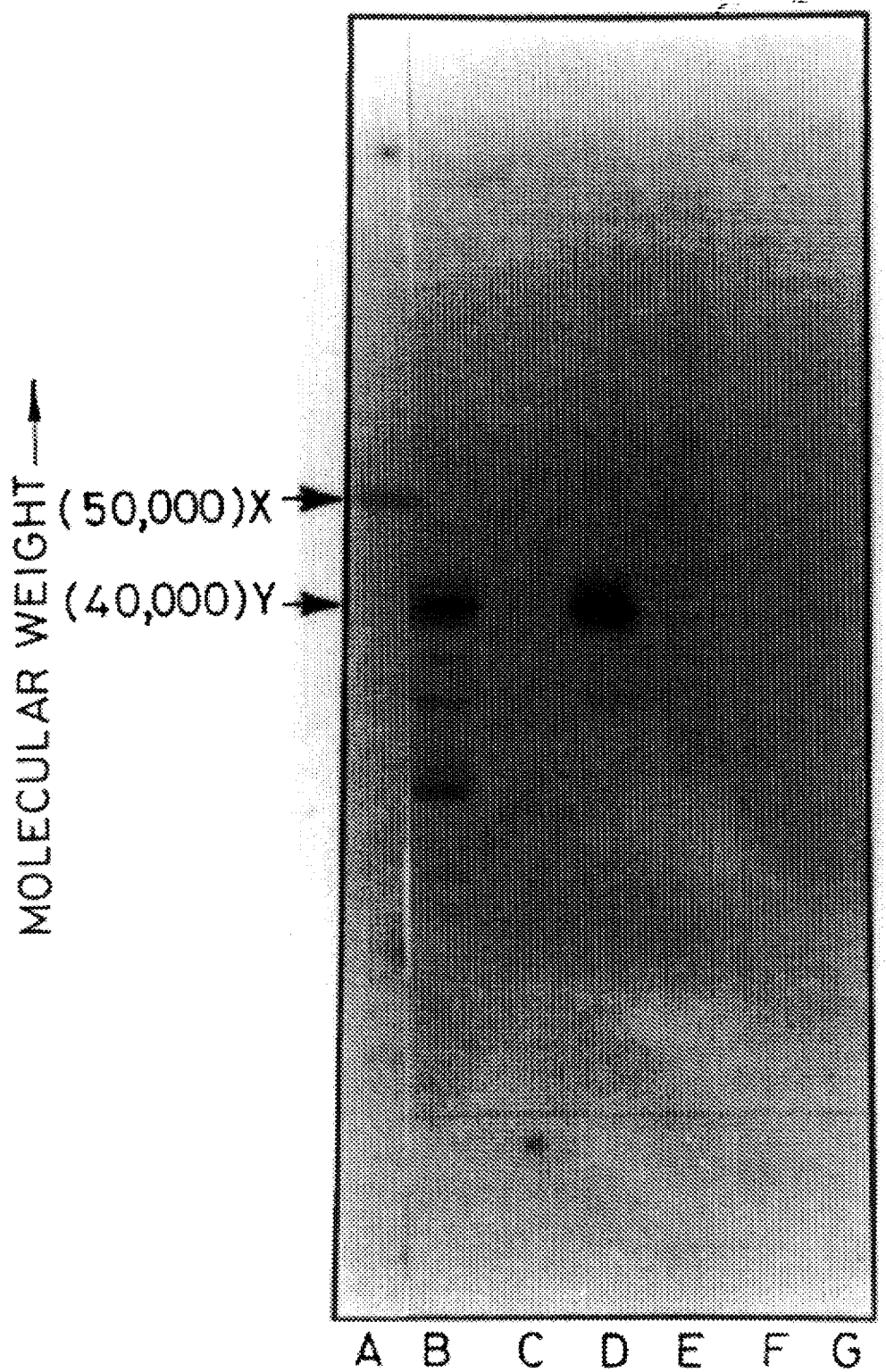

DNA ENCODING LIPASE FROM HUMAN GASTRIC MUCOSAL TISSUE

This application is a division of application Ser. No. 08/097,619, filed Jul. 27, 1993, now abandoned, which is a continuation of application Ser. No. 07/996,488 filed Dec. 28, 1992, now abandoned, which is a continuation of 07/750,704 filed Aug. 20, 1991 now abandoned, which is a continuation of 07/554,062 filed Jun. 26, 1990, now abandoned, which is continuation of 06/865,564 filed Apr. 21, 1986, now abandoned.

BACKGROUND OF THE INVENTION

This invention relates to a polypeptide and a composition comprising the polypeptide. The polypeptide may be produced by the technique of recombinant DNA biotechnology.

The lipolysis of dietary fat is an important feature of the digestive systems of higher animals. The digestive process is made possible by enzyme catalysed hydrolysis of triglycerides to produce a mixture of monoglycerides, diglycerides, glycerol and free fatty acids as the fats pass through the digestive tract. The hydrolysis products are able to pass through the epithelial membrane of mucosal cells lining the gut. Once absorbed they are used to resynthesise triglycerides which are incorporated in chylomicrons. Chylomicrons are transported by the lymph system away from the site of absorption. The enzymes carrying out triglyceride hydrolysis are termed lipases and are secreted into the gastrointestinal tract (Desnuelle, P (1972)). The Enzymes Vol. VII, 3rd Edition, Acad. Press New York and London, and Verger, R. (1980) Methods in Enzymology 64, 340–392).

An enzyme involved in triglyceride hydrolysis is pancreatic lipase (ED 3.1.1.3). The pig is a convenient source of enzyme and pig pancreatic lipase has been extensively studied. It is present at approximately 2.5% of the total proteins in pig pancreatic juice, and has been purified to homogeneity (Verger, R. et al (1969) Biochem Biophys Acta 188, 272–282). The complete amino acid sequence of the enzyme has been determined (De Caro, J. et al (1981) Biochem Biophys Acta 671, 129–138). The enzyme comprises a protein portion of 449 amino acids (MW 49859) with a carbohydrate portion (MW about 2000) attached to an Asn residue at position 166 in the amino acid sequence. The total molecular weight of the enzyme is therefore approximately 52000. The catalytic activity of pancreatic lipase is complex since there exists a phase separation between the soluble enzyme and the insoluble triglyceride substrate. In order for the enzyme to interact with the substrate a coenzyme known as colipase is necessary. Colipase is a low molecular weight protein which adsorbs to the solution/lipid interface and then acts as an anchor for lipase, allowing interaction between the enzyme and its lipid substrate.

Pancreatic lipase may be assayed by a variety of techniques (see Desnuelle and Verger as above) involving the measurement of the disappearance of the triglyceride or the appearance of free fatty acid or glycerol. Radioactive labelling, proton release during hydrolysis, and the effect of lipase on the physical properties of a lipid monolayer may also be used to assay lipase activity. In all cases pancreatic lipase is optimally active in the neutral-alkaline pH range (i.e. pH7–pH9) (see Verger et al as above). The enzyme is highly sensitive to acid pH and is rapidly inactivated at low pH.

A number of lipid malabsorbtion illnesses of the human body are characterised by reduced levels of pancreatic lipase secretion.

About eighty percent of individuals suffering from cystic fibrosis suffer from pancreatic insufficiency. Pancreatic lipase insufficiency manifests itself shortly after birth and continues throughout the lifetime of the patient.

Pancreatitis is a condition in which the action of the pancreas is impaired. Pancreatitis often develops in chronic alcoholics who, as a result, suffer from malabsorption of fats and consequent malnutrition.

A developing foetus is dependent upon high carbohydrate nutrition, and has a poorly developed pancreatic function producing low levels of pancreatic lipase. At birth the high carbohydrate nutrition of the foetal period is replaced by a high fat diet as the infant begins to take its mothers milk. Fats account for about half an infant's calories input. The pancreatic function, even in infants that are carried to full term, is not fully productive and infants, especially those born prematurely, may suffer from inadequate fat digestion leading to appreciable steatorrhea (passage of undigested fat in the faeces) and to a resulting loss of energy.

The present treatment of patients suffering from a deficiency of pancreatic lipase is the oral administration of very large doses of a crude preparation of pig pancreas enzyme. Pancreatic lipase is inactivated by low pH. Such conditions are prevalent in the stomach, with the result that orally administered pancreatic lipase is virtually completely inactivated on the passage through the stomach to the gut. Therefore this effect cannot be completely overcome by the use of large doses of enzyme. The large doses administered are inadequate for most patients, are impure and unpalatable. Certain tablets have been formulated which pass through the acid regions of the stomach and discharge the enzyme only in the relatively alkaline environment of the jejunum (Gow, R. et al (1981) the lancet Vol. II 8255, 1070–1074). However, many patients suffering from pancreatic disorders have an abnormally acid jejunum and such tablets may fail to discharge the enzyme and may therefore be ineffective.

There is a great need for a preparation of a lipase which may be orally administered to patients suffering from a deficiency of pancreatic lipase.

Published European patent application No. EP-A1-0131418 describes one such preparation comprising lingual lipase, an acid stable lipase originating from the tongue and capable of carrying out lipolysis in the lumen of the stomach. The present invention provides a preparation comprising a gastric lipase, a lipase originating from stomach tissue and also capable of carrying out lipolysis in the stomach lumen.

Prior to the present invention only preliminary studies on the existence and enzymological properties of human gastric lipase had been carried out. A review (Desnuelle, P. (1971), the Enzymes, Vol. VII, 3rd Edition, Acad. Press, N.Y. and London) stated that "the case of gastric lipase is not yet firmly established".

A series of reports by Szafran, Z. et al. (Enzyme, (1983) 30, 115–121; digestion (1978) 18, 310–318; and Enzyme (1978), 23, 187–193) indicate that gastric mucosa secretes an acid stable lipase. The experimental basis of this rests on comparative zymograms (polyacrylamide gels of protein extracts which are stained for enzymic activity) of gastric mucosa tissue and gastric aspirates together with studies on the apparent co-secretion of the pepsin, hydrogen ions and lipase activity from the stomach mucosa after treatment of the patient with pentagastrin (pentagastrin stimulates secretion of fluid and enzymes from the gastric mucosa). Both gastric juice and stomach mucosa produce closely similarly zymogram patterns when stained for lipase activity. However, zymograms of duodenal tissue are markedly different from stomach mucosal tissue indicating that duodenal tissue does not secrete this gastric lipase. Measurement of pepsin, hydrogen ion and lipase activity appearing in human stomach aspirates after continuous administration of pentagastrin in graded doses showed an apparent coupled secretion. No information on the protein chemistry of the lipase from gastric mucosa was provided in this work.

SUMMARY OF THE INVENTION

A lipase has been purified to homogeneity from human gastric aspirates (the liquid contents of the stomach lumen (see Tiruppathi, C. and Balsubramanian, K. A. Biochim, Biophys, Acta. (1982) 712, 692–697).

This enzyme has the following properties:

a. Molecular weight approximately 45,000.

b. Capable of carrying out lipolysis under acidic conditions (between pH 3.5–6.5)

Hence, the enzyme resembled lingual lipase and its origin was attributed to the lingual serous glands by these authors. However, from the above, it is also possible that an unknown fraction of this enzyme originated from the human gastric mucosa. The lipase present in human gastric aspirates may therefore be a mixture of lingual and gastric enzymes. We have now shown that human gastric mucosa secretes a lipase. This human gastric lipase has been shown to be generally similar in chemical composition to lingual lipase but to differ in particular structural respects.

All the work reported above on gastric lipase has been exclusively of an academic nature, and no suggestion has been made of using gastric lipase for the treatment of lipase deficiency. We believe that gastric lipase can be so used, but it is only economic to do so if gastric lipase can be produced on a large scale and at relatively little expense. It is clearly impractical to do this by extraction from animal or human tissue.

We provide gastric lipase in such commercially worthwhile amounts by producing it, in accordance with the invention, using recombinant DNA techniques.

According to a first aspect of the present invention we provide a gastric lipase protein for use in the treatment of lipase deficiency.

As used herein the term "gastric lipase protein" denotes an authentic mammalian gastric lipase or an authentic mammalian gastric lipase modified or substituted to provide a functionally equivalent protein. The gastric lipase protein may, for example, comprise a mammalian gastric lipase protein with an N-terminal methionine amino acid residue (a methionine-gastric lipase protein). Preferably the gastric lipase protein is a human gastric lipase protein.

The gastric lipase protein is advantageously produced by a recombinant DNA technique.

In a second aspect of the invention we provide a process for the productions of a methionine-gastric lipase protein comprising producing the protein in a host organism transformed with a vector including a gene coding for the methionine-gastric lipase protein.

To obtain expression of a DNA sequences, DNA sequence must possess a 5' ATG codon and the corresponding polypeptide therefore possesses an N-terminal methionine amino acid. As used herein the term "methionine-gastric lipase protein" denotes an authentic gastric lipase (or an authentic mammalian gastric lipase, modified or substituted to provide a functionally equivalent protein) having an N-terminal methionine amino acid residue. Preferably the methionine residue is adjacent the N-terminal amino acid of an authentic gastric lipase but may be separated therefrom by one or more amino acids provided that the protein possesses gastric lipase functional activity. Preferably the host organism is a bacterium (for example *E. coli*) or a yeast (for example *Saccharomyces cerevisiase*).

In a third aspect of the invention we provide a process for the production of a gastric lipase protein comprising producing a gastric lipase precursor protein in a host microorganism transformed with a vector including a DNA sequence coding for the precursor protein and cleaving the precursor protein to produce the gastric lipase protein.

Preferably the gastric lipase precursor protein is a pregastric lipase protein and the host organism is a host organism capable of cleaving the pregastric lipase protein to produce the gastric lipase protein. Most preferably the host microorganism cleaves the pregastric lipase and may export the gastric lipase protein to the culture medium.

In an alternative form of the third aspect of the invention the precursor gastric lipase protein is a fusion protein comprising a heterologous protein and a gastric lipase protein. The heterologous protein may be all or a part of a protein capable of production, desirably at a high level, in the host organism. Suitable such proteins include β-galactosidase chloroamphenicol acetyl transferase (CAT) and the product of the trpE gene. The fusion protein preferably includes a site susceptible to selective chemical or enzymic cleavage between the heterologous protein and the gastric lipase protein. The heterologous protein may be a yeast signal sequence and the host organism may be yeast. In this preferred embodiment the yeast host organism advantageously cleaves the fusion protein to produce a mature gastric lipase protein.

In a fourth aspect of the invention we provide a progastric lipase protein.

In a fifth aspect of the invention we provide a methionine-gastric lipase protein.

In a sixth aspect of the invention we provide a fusion protein comprising a heterologous protein and a gastric lipase protein.

In a seventh aspect of the invention we provide a DNA sequence coding for at least the amino acid sequence of a gastric lipase protein. Preferably the DNA sequence codes for a protein of the fourth, fifth, or sixth aspect of the invention.

We further provide a DNA sequence coding for at least the amino acid sequence of human gastric lipase or human pre gastric lipase as shown in FIG. 3 of the accompanying drawings. Preferably the DNA sequence is as shown in FIG. 3.

In an eighth aspect of the invention we provide a vector including a DNA sequence of the seventh aspect of the invention. The vector is adapted for use in a given host microorganism by the provision of suitable selectable markers, promoters and other control regions as appropriate.

In a ninth aspect of the invention we provide a host microorganism transformed with a vector according to the eighth aspect of the invention. The host microorganism may be any organism which may be transformed by a vector including a DNA sequence coding for a gastric lipase protein such that expression of the DNA sequence occurs. Suitable such host organisms include bacteria (for example *E.coli*), yeasts (for example *Saccharomyces cerevisiae*) and mammalian cells in tissue culture. Preferably, where the host organism is a bacterium or a yeast the vector includes a gene coding for methionine-gastric lipase or a fusion protein, and when the host organism is a mammalian cell in tissue culture the vector preferably includes a DNA sequence coding for pregastric lipase.

In a tenth aspect of the invention we provide a pharmaceutical composition comprising a gastric lipase protein and a pharmaceutically acceptable excipient. Preferably the lipase protein is a human gastric lipase produced by a process of the second or third aspect of the invention. The pharmaceutical composition is provided for use in the treatment of lipase deficiency. Preferably the composition is formulated for oral administration.

The composition may be in unit dosage form, for example as a tablet, capsule or dragee.

To produce a unit dosage form the gastric lipase, in a suitable form, may be mixed with a solid pulverulent non-pharmaceutically active carrier such as lactose, saccharose, sorbitol, mannitol, starch, cellulose derivatives or gelatine or any other such excipient. A lubricant such as magnesium stearate, calcium stearate or polyethylene glycol wax may be added. The resulting composition is compressed to form a unit dosage form. The unit dosage form may be coated with a concentrated sugar solution which may contain additives such as talc, titanium dioxide, gelatins or gum arabic. The unit dosage form may be coated with lacquer. Dyestuffs may be added to the coating to facilitate identification of the unit dosage form. Soft or hard capsules may be used to encapsulate gastric lipase as a liquid or solid preparation.

Alternatively, the gastric lipase may be formulated in a liquid form. To produce a liquid form of the preparation the gastric lipase in a suitable form may be added to a liquid carrier. The carrier may be, for example, a syrup or a suspension. The liquid form may contain colouring compounds, flavouring compounds, sweetening compounds, and/or thickening compounds.

In a further aspect of the invention we provide a process for the production of a pharmaceutical composition comprising bringing a gastric lipase protein into association with a pharmaceutically acceptable carrier. In a yet further aspect of the invention we provide a method for the treatment of lipase deficiency comprising administering an effective amount of a gastric lipase protein.

The invention also provides plasmids PGL17, pCML1 and pMG197.

BRIEF DESCRIPTION OF THE DRAWINGS

In the following description a protocol is described for the production of gastric lipase using recombinant DNA technology with reference to the following drawings in which:

FIGS. 2(a), 2(b) and 2(c) show a restriction endonuclease map of plasmids pGL17

((a) shows the restriction map, (b) indicates the limits of the DNA sequence shown in FIG. 3 and (c) indicates the location of the human gastric lipase protein sequence with the thick line representing the pre or signal sequence), FIG. 9 shows a western bloc analysis of human gastric lipase produced in yeast transformed with plasmid pYC3, FIG. 10 shows an SDS-PAGE analysis of human gastric lipase produced in yeast transformed with plasmid pYC3.

DESCRIPTION OF THE PREFERRED EMBODIMENT

The strategy used was to first purify human gastric lipase from human gastric aspirates. The purified enzyme was subjected to N-terminal amino acid sequencing, structural characterisation and a polyclonal antiserum raised. The DNA sequence for this enzyme was cloned by screening a cDNA library made from human stomach tissue with a probe consisting of the highly homologous rat lingual lipase. The complete nucleic acid/protein sequence of human gastric lipase was determined. The present specification describes how this human gastric lipase clone is expressed in an appropriate microorganism or animal cell in tissue culture to produce a recombinant human gastric lipase product.

Purification of Human Gastric lipase from Human Stomach Aspirates

Figure 1:
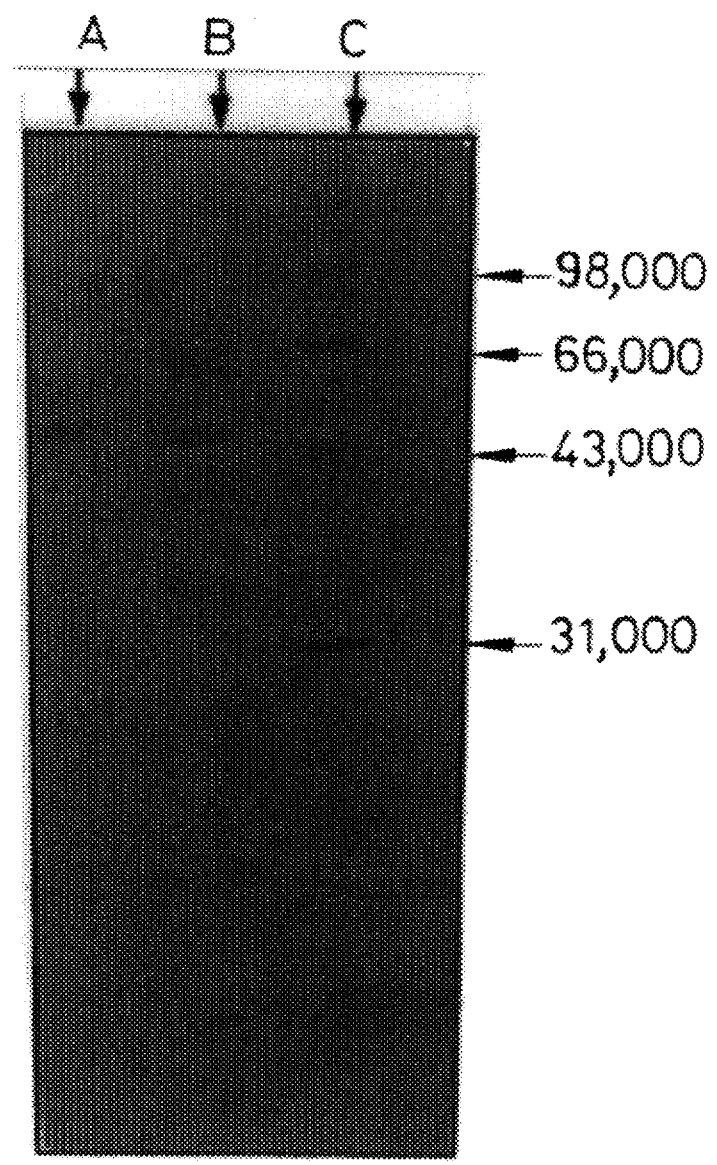
FIG. 1 shows an SDS polyacrylamide gel of two preparations of human gastric lipase (Lane A—purified human gastric lipase, Lane B—partially purified extract of human gastric lipase, Lane C—standard molecular weight markers)

Human gastric lipase was purified from gastric aspirates by the method of Tiruppathi et al (1982) Biochim. Biophys. Acta. 712 692–697. This procedure produced pure human gastric lipase with a molecular weight of approximately 50,000 as judged by SDS PAGE. (Lammeli (1970) Nature 277 68–685), FIG. 1 shows a polyacrylamide SDS gel of human gastric lipase preparations. Lane A, purified human gastric lipase (approximately 5 µg) and Lane B, a partially purified extract of human gastric aspirate (approximately 10 µg), Lane C, a series of standard molecular weight markers. The enzyme had an activity of approximately 600 lipase units per mg (unit-micromoles of free fatty acid formed per minutes at 37° C.).

Preparation of polyclonal Rabbit Anti-Human Gastric Lipase Antiserum

Approximately 100 µg of a preparation of electrophoretically pure human gastric lipase isolated as described above was taken up in 1 ml complete Freund's adjuvant and injected into a rabbit. After 14 days the innoculation was repeated using incomplete Freund's adjuvant. The rabbit was bled to produce antiserum after 28–30 days and at subsequent intervals. The titre of the antiserum was determined by standard immunological procedures.

Characterisation of Authentic Human Gastric Lipase
Determination of Molecular Weight Human gastric lipase, purified to homogeneity and subjected to electrophoresis in SDS polyacrylamide gels migrated as a single band with an apparent molecular weight of approximately 50,000 (FIG. 1). Gel filtration of impure human gastric lipase on Sephadex® G150 resulted in a calculated molecular weight in approximate agreement with that obtained by polyacrylamide gel electrophoresis. A molecular weight of 45,000 has been estimated by Tiruppathi et al. (1982), see above, using gel filtration on Sephadex® G100. It is therefore concluded that the purified human gastric lipase is active as a monomer of approximately 50,000 molecular weight.

N-Terminal Amino Acid Sequence and Total Amino Acid Composition of Human Gastric Lipase The N-terminal amino acid sequence of purified human gastric lipase was determined by the method of Smith, M. A. et al (1982) Biochemical Journal 207, 253–260.

N.-Terminal Amino Acid Sequence of Human Gastric Lipase

```
1                                    10
Leu Phe Gly Lys Leu — Pro Thr Ser Pro Glu Val Thr Met
                    20
— Ile Ser Gln Met Ile Thr Tyr Trp

— Tyr — Asn Gln
```
(a dash indicates an amino acid not determined)

TABLE 1

Partial Amino Acid Composition of Human Gastric Lipase

| Residue | nMoles Amino Acid Eluted* | Total amino acids predicted from DNA Sequence |
|---|---|---|
| Asp + Asn | 52.4 | 48 |
| Thr | 19 | 19 |
| Ser | 28.8 | 26 |
| Glu + Gln | 38.2 | 29 |
| Pro | 24.9 | 22 |
| Gly | 29.5 | 23 |
| Ala | 28.8 | 24 |
| Val | 28.7 | 24 |
| Met | 10.6 | 9 |
| Ile | 22.2 | 22 |
| Leu | 36.0 | 33 |
| Tyr | 21.5 | 21 |
| Phe | 25.5 | 25 |
| Lys | 21.2 | 22 |
| His | 11.7 | 10 |
| Arg | 10.6 | 10 |

*Cys, Trp were not determined.

Determination of the Presence of Glycosylation in Human gastric lipase

The presence of asparagine linked N-glycosylation was established by digestion of purified human gastric lipase with Endoglycosidase H (Endo-B-N-acetylgucosaminidase H) from *streptomyces plicatus*. A 1 mg/ml solution of human gastric lipase in 50 mM sodium acetate pH 5.5, 1 mM Phenyl methyl sulphonyl fluoride, 10 uM pepstatin A containing 50 units/ml Endoglycosidase H was incubated at 37° C. Alternatively, human gastric lipase was boiled in 0.4% SDS and diluted to 0.1% SDS before incubation as above. In both cases the human gastric lipase digestion products were separated on SDS PAGE and visualised by Coomassie Blue staining. Digestion of human gastric lipase with Endoglycosidase H resulted in the generation of a series of lower molecular weight forms with a minimum molecular weight of approximately 41,000. Endoglycosidase H digestion results in the removal of N linked carbohydrate moieties from glycoproteins containing these residues. This cleavage produces an apparent lowering of the molecular weight of the deglycosylated protein. This lowering of molecular weight maybe visualised by increased mobility of the deglycosylated protein on SDS PAGE. That Endoglycosidase treatment of human gastric lipase results in an apparent decrease of molecular weight from approximately 50,000 to approximately 41,000 indicates that approximately 20% of the enzyme (by weight) is composed of carbohydrate.

Cloning of Human Gastric Lipase

A DNA sequence encoding human gastric lipase was isolated from a cDNA clone bank made from mRNA prepared from a sample of human stomach tissue. Human gastric lipase clones were indentified by homology with a cDNA clone of rat lingual lipase previously obtained as described in published European application EP-A-0131418. A freshly obtained section of human stomach wall tissue approximately 2 cm wide was stored in liquid nitrogen. The section contained complete mucosal, muscle and serosa layers. RNA was prepared by guanidinium isothiocyanate extraction of the frozen ground complete tissue (Maniatis et al (1982) "Molecular Cloning—A Laboratory Manual". Cold Spring Harbor Laboratory). Polyadenylated RNA was isolated from this by oligo-dT cellulose chromatography (Harris, T. J. R. et al. (1975) J. Gen. Virol 29 299–312).

The presence of an mRNA species encoding an acid stable lipase was suggested by Northern Blot analysis (Thomas, P. S. (1980) PNAS USA, 77 5201–5205). By this technique polyadenylated stomach RNA was separated on the basis of molecular weight by gel electrophoresis and probed with a cDNA clone of the rat lingual lipase DNA sequence labelled by nick translation (Rigby P. W. J. et al J. Mol. Biol. 113, 237–251). The probe used was an EcoRV to Aha III fragment of pLL10 (see above). This labelled DNA sequence specifically hybridised with a mRNA species with an apparent size of approximately 1500 bases. This mRNA species was of a size capable of encoding a protein of the apparent size of human gastric lipase together with untranslated 5' and 3' sequences of such a message.

cDNA was prepared to the human stomach mRNA. First strands were synthesised by poly(dT) priming and elongation by AMV reverse transcriptase (Retzel, E. F. et al (1980) Biochemistry 19 513–516). Second strands were synthesised by the action of RNase H, *E.coli* DNA polymerase I and *E.coli* DNA ligase as described (Gubler, V. and Hoffman, B. (1983) Gene 25, 263–269). The double stranded cDNA was tailed at the 3' ends with poly(dT) (Villa-Komaroff et al (1978) PNAS USA, 75: 3727). Tailed fragments were annealed into pBR322 which had been cleaved and poly(dG) tailed at the PstI site. These hybrids were transformed into *E.coli* DH1 competent for transformation (Maniatis et al (1982) "Molecular Clong—A laboratory Manual". Cold Spring Harbor Laboratory). The transformants were screened by colony hybridisation on nitrocellulose filters (Hanahan, D. and Meselson, M (1980) Gene 10 63–67). The hybridisation probe was the NDA fragment containing the coding region for rat lingual lipase labelled by nick translation (Rigby, P. W. J. et al (1977) J. Mol. Biol. 113 237–252).

Putative human gastric lipase clones were mapped for restriction endonuclease cleavage sites (FIG. 2) and subjected to DNA sequencing (Sanger, F. S., et al (1977) PNAS USA 74 5463–5467; Smith, A. J. H. (1980) "Methods in Enzymology" Academic Press 65 560–580) using a synthetic single-stranded oligodeoxyribonucletide primer which hybridised to a region just 3' to the cloned segment. Clones were shown to encode the lipase by sequence homology with the rat lingual lipase cDNA sequence and comparison of the predicted sequence from the cDNA clones with the N-terminal amino acid sequence of native human gastric lipase isolated from stomach aspirate (Table 1 and FIG. 3). One clone was identified (pGL17), approximately 1450 bp long containing the entire coding sequence for the gastric prelipase. The 5' end of the clone was shown to be within 20 nucleotides of 5' terminal nucleotide of the message. This was demonstrated by the sequence obtained from the primer extension. In this technique a synthetic oligodeoxyribonucleotide primer was hybridised specifically to a region of the human gastric lipase mRNA encoding the N-terminal protein sequence. This primer was extended to the 5' end of the mRNA and the sequence determined. A restriction endonuclease map of pGL17 was constructed and is shown in FIG. 2, line a. Numbers below this line relate to the base numbering given in FIG. 3. FIG. 2, line b indicates the limits of the DNA sequence provided in FIG. 3. The location of the human gastric lipase protein sequence is shown in FIG. 2, line c. The thick line labelled "pre" refers to the location of the "pre" or signal sequence of human gastric lipase. (In FIG. 2 the restriction site abbreviations are as follows: P=PstI, E=EcoRV, R=EcoRI, A=AluI, B-BalI, Bc=BclI, and Ah=AhaIII).

Figure 3:
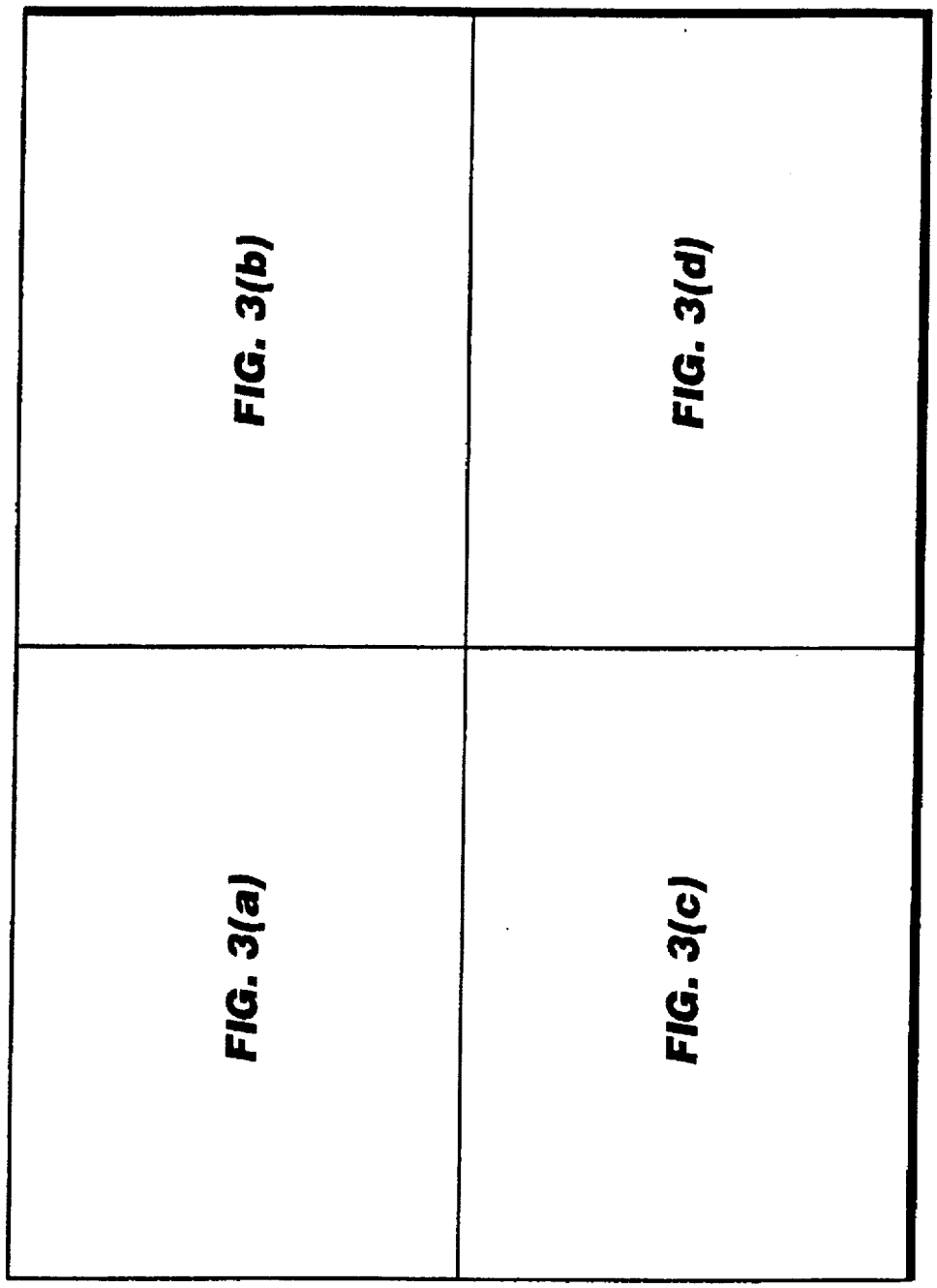
FIGS. 3(a), 3(b) and 3(d) show the DNA sequence of the coding strand of the DNA sequence encoding human pre gastric lipase and the associated amino sequence.

The DNA sequence of the coding strand of the pre human gastric lipase gene is shown in FIG. 3. Numbers below the DNA sequence represent the base number. Base 1 is the first nucleotide of the cloned human gastric lipase sequence in pGL17. An "*" indicates the stop codon TAG which is followed by a 3' untranslated region. Letters immediately above the bases represent the derived amino sequence, using the conventional single letter amino acid code (i.e. A=alanine, R=arginine, N=asparagine, D=aspartic acid, C=cysteine, E=glutamic acid, Q=glutamine, G=glycine, H=histidine, I=isoleucine, L=leucine, K=lysine, M=methionine, F=phenylalamine, P=proline, S=serine, T=thronine, W=tryptophan, Y=tyrosine and V=valine).

Underlined letters above the derived amino acid sequence represent the N-terminal amino acid sequence obtained directly from purified human gastric lipase. Spaces in the directly obtained amino sequence represent undetermined amino acids. Amino acids −19 to −1 represent a putative signal sequence and +1 to 379, the amino acid sequence of the mature DNA sequence. Broken underlining indicates the potential glycosylation sequence. The amino acid sequence predicted from the DNA sequence indicates that mature human gastric lipase consists of a 379 amino acid protein. The predicted molecular weight of this mature protein is 43,162 which is in close agreement with the molecular weight determined for the deglycosylated enzyme by SDS PAGE. The total amino acid composition of the mature enzyme produced from the DNA sequence is compared with that obtained directly from the isolated protein in Table 1. Mature human gastric lipase contains at least 3 potential sites for glycosylation (e.g., of the general form X Asn X Thr or Ser). Human gastric lipase is 70 amino acids shorter than porcine pancreatic lipase and bears little sequence homology or amino aid composition similarity to this enzyme. However, close homology does exist between human gastric lipase and porcine pancreatic lipase in the region of the essential serine-152 of porcine pancreatic lipase. The serine is thought to participate in the interfacial fixation of pancreatic lipase to lipid (Guidoni, A. et al 1981, Biochim. Biophys. Acta. 660, 148–150) and reacts with micellar diethyl-p-nitrophenyl phosphate (Rouard, M. et al 1978, Biochim, Biophys. Acta. 530, 227–235). It is present in the sequence: 152 Gly- His- Ser- Leu- Gly in Porcine pancreatic Lipase and in a closely equivalent position in the primary amino acid sequence:

$$153$$
$$Gly — His — Ser — Gln — Gly$$

Another point of similarity, close to this essential serine residue, is the single glycosylation position in procine pancreatic lipase (Asn-166) which appears to be present in Asn-166 in human gastric lipase.

Mature human gastric lipase has a striking amino acid sequence homology (approximately 76%) with rat lingual lipase (see published European patent application EP-A1-00131418) which corresponds to U.S. Ser. No. 709,956 However, the amino acid sequence of the signal sequences of human gastric lipase and rat lingual lipase do show certain differences. Only the 5 N-terminal and 2 C-terminal amino acid residues of the signal sequences are homologous. Human gastric lipase contains one less cys residue and one less potential glycosylation site than rat lingual lipase. The retained cys residues and glycosylation sites are in virtually equivalent positions in the primary amino sequence of human gastric lipase and rat lingual lipase.

Expression of human gastric lipase in (i) E.coli (ii) Yeast (iii) Tissue cultured animal cells (i) E.coli A plasmid vector for the expression of mature methionine-human gastric lipase (hereinafter referred to simply as human gastric lipase) was constructed based on the dual replication origin temperature inducible vector system described in published European patent application EP-A1-0121386 which corresponds to U.S. Pat. No. 5,015, 573. (The disclosures of which are incorporated herein by reference). This plasmid was constructed using the complete prelipase DNA sequence on a PstI to Aha III DNA fragment of the cloned DNA sequence. The 3' end of the DNA sequence was isolated as an AccI to BglII fragment, and the 5' end as a FokI to AccI fragment (see FIG. 4). To this a pair of linkers were added at the 5' FokI end. These oligonucleotides reconstructed and 5' end of the lipase gene, added an ATG start site, provided a BglII site in the Shine-Dalgarno-ATG region and provided a ClaI site for cloning into pCT54 (described in Emtage et al Proc. Natl. Acad. Sci. (1983) 3671–3675). pCML1 was constructed by digestion of pCT54 with ClaI and BclI followed by a three way ligation carried out as follows:

(1) ClaI/BclI vector (2) ClaI/AccI 5' end (3) AccI/BglII 3' end

This yielded pCML1 with a Shine Dalgarno ATG distance of 14 nucleotides.

Figure 4:
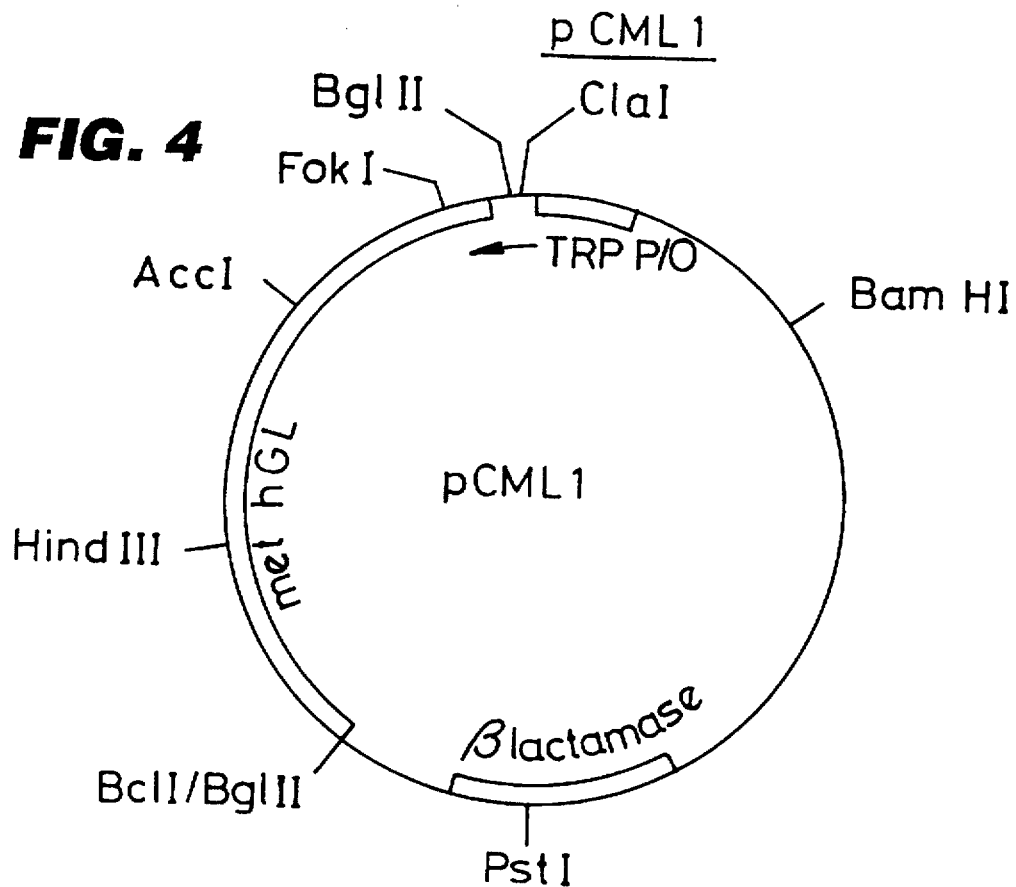
FIG. 4 shows a restriction endonuclease map of plasmid pCML1.

A restriction endonuclease map of plasmid pCML1 is shown in FIG. 4. The nucleotide sequence in the region of the trp promoter and start of the DNA sequence encoding human gastric lipase is shown below:

| ClaI | | BglII | |
|---|---|---|---|
| ACGTAAAAAGGGTATCGATAGATCTATGTTGTTT..... | | | |
| Shine-Dalgarno sequence | | Met Leu Phe......... human gastric lipase DNA sequence | |

Figure 5:
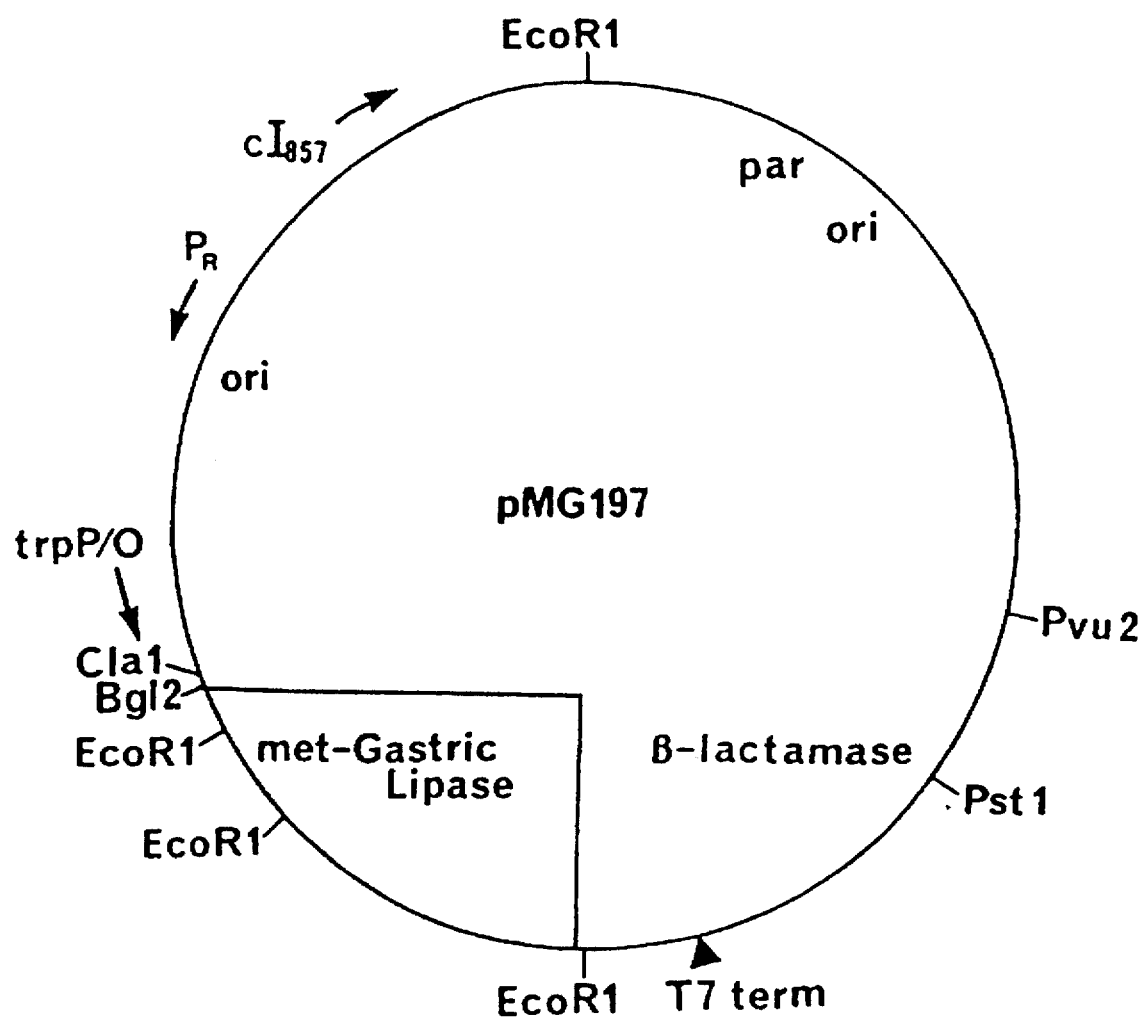
FIG. 5 shows a restriction endonuclease map of plasmid pMG197.

The plasmid used for expression of human gastric lipase in E.coli was termed pMG197. This plasmid was based on pMG165, a dual replication origin vector described in published European patent application EP-A1-0121386 (which corresponds to U.S. Pat. No. 5,015,593, the contents of which are incorporated herein by reference). pMG197 was constructed by digestion of pCML1 with BamHI and PstI and the fragment bearing the human gastric lipase DNA sequence isolated. pMG171 is pMG165 with the Bam HI site destroyed and Hind III/Sal I site removed and replaced with a Bam HI site (pMG165 is as described in published European patent application EP-A1-0121386) (which corresponds to U.S. Ser. No. 6,763,392, U.S. Pat. No. 5,015, 593, the contents of which are incorporated herein by reference was also digested with BamHI and PstI and the human gastric lipase DNA sequence containing fragment inserted to form pMG197 (FIG. 5). This plasmid was isolated and transformed into E.coli E103(S).

E.coli containing pMG197 was grown as described in published European patent application EP-A1-0121386 (which corresponds to U.S. Pat. No. 5,015,593 the contents of which are incorporated herein by reference) in a 10 liter fermentation vessel, the cells harvested by centrifugation and stored at −20° C.

Figure 6:
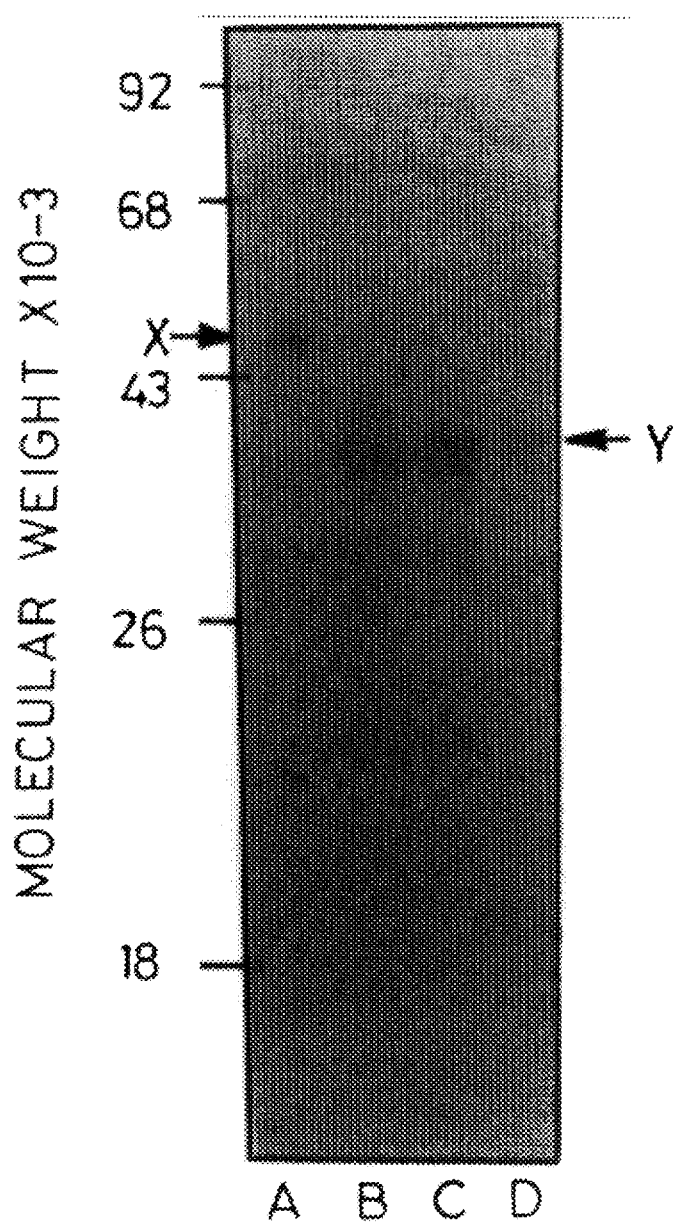
FIG. 6 shows a western blot analysis of human gastric lipase produced in E.coli transformed with plasmid pMG197.
Figure 6:
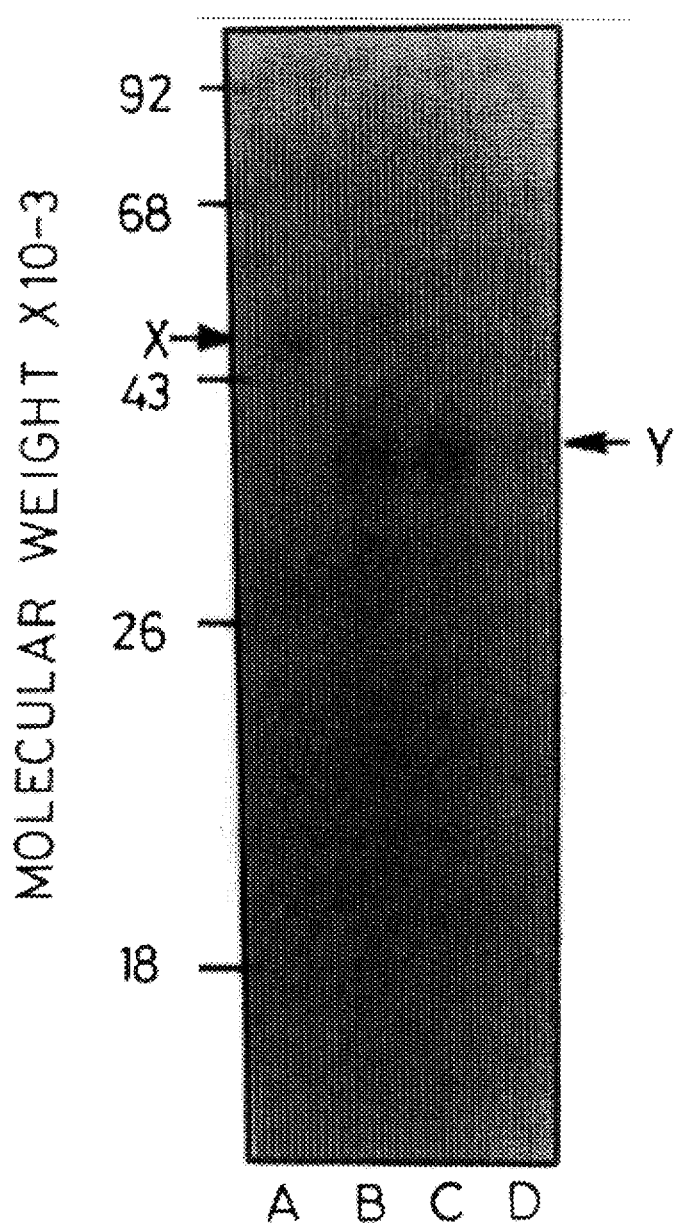

A "Western blot" analysis on total proteins present in E103(S)/pMG197 was carried out as described by Burnette, (Burnette, W. N. (1981) Anal. Biochem. 112, 195–203). In this analysis total proteins were separated by SDS-PAGE and transferred to a nitrocellulose membrane. Human gastric lipase was detected using polyclonal antiserum to natural human gastric lipase and the complex labelled with $^{125}$I-Protein A (FIG. 6).

The arrow labelled X (lane A) indicates the position of migration of natural human gastric lipase. The arrow labelled Y indicates the position of a novel protein produced in E103(S)/pMG197 after a temperature induction carried out as described in published European patent application EP-A1-0121386 (which corresponds to U.S. Ser. No. 676392, U.S. Pat. No. 5,015,573 the contents of which are incorporated herein by reference). Lanes B and C correspond to total proteins extracted from cells harvested 3 hours and 2 hours after temperature induction. Uninduced cells are shown in Lane D. This analysis indicated that E103(S)/pMG197 expressed human gastric lipase as a prominent protein migrating with an apparent molecular weight of approximately 38,000. The discrepancy between the apparent molecular weights of natural human gastric lipase (approx. 50,000) and recombinant human gastric lipase (approx. 38,000) could be due to the inability of E.coli to carry out glycosylation. Unglycosylated human gastric lipase has a molecular weight of 43,162 as predicted by amino acid sequence derived from the DNA sequence of the cloned gene.

Human gastric lipase was partially purified from E.coli and solubilised as described below. 10 g of frozen cell paste of E103(S)/pMG197 was resuspended in 50 ml of 50 mM Tris pH8, 50 mM Nacl, 1 mM EDTA and 0.1 mM PMSF. All manipulations were carried out at 4° C. unless indicated otherwise. Suspended cells were passed three times through a French Press operating at 1,500 psi. The suspension of broken cells was centrifuged at 12,000 for 5 minutes. Samples of the supernatant were retained for analysis and the pellet fraction (containing the human gastric lipase product in an insoluble form) resuspended in 50 mM Tris pH8, 10 mM EDTA and 0.5% Triton® X-100. The resuspended pellet fraction containing the insoluble human gastric lipase product was recentrifugated as described above. Insoluble human gastric lipase was solubilised by urea or alkali in a manner similar to that described in British Patent Specification GB2100737B and in British patent applications GB2129810A and GB2138004A. Insoluble human gastric lipase was dissolved in 50 mM Tris pH8, 8M urea at room temperature at a final protein concentration of approximately 1 mg/ml. Denaturant was removed by dialysis against a solution of 50 mM sodium carbonate/bicarbonate buffer at pH10.7. Precipitated protein was removed by centrifugation.

Figure 7:
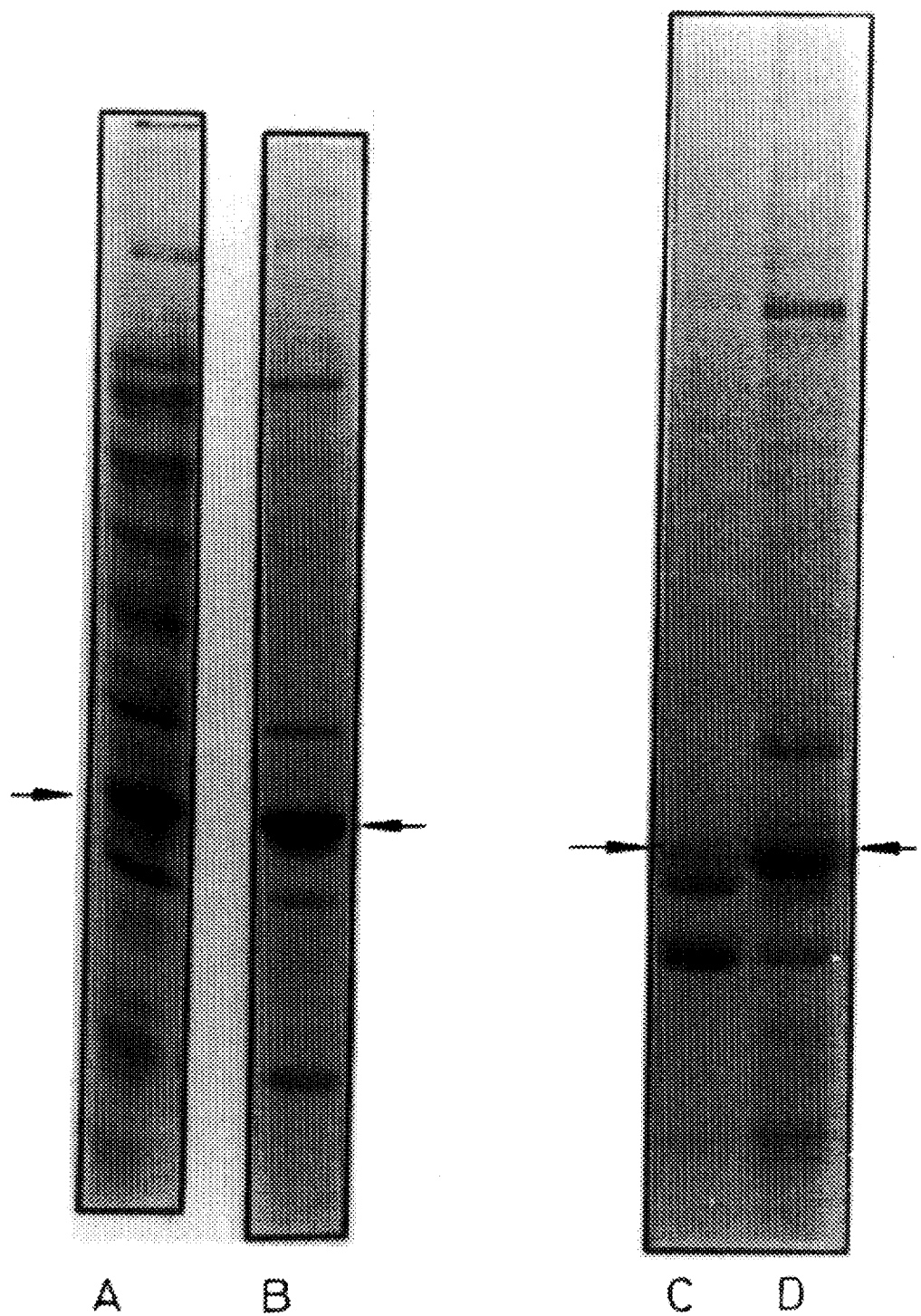
FIG. 7 shows an SDS-PAGE analysis of human gastric lipase produced in E.coli transformed with plasmid pMG197.

An SDS-PAGE analysis of human gastric lipase expression and solubilisation is shown in FIG. 7. Arrows indicate the expressed human gastric lipase protein. Total proteins from E103(S)/pMG197 are shown in Lane A. Quantitative gel scanning indicated that human gastric lipase was expressed as approximated 8% of total E.coli proteins. Lane B shows the composition of the proteins present in the washed insoluble cell extract. Human gastric lipase constituted a major proportion of the insoluble protein present in the pellets produced by centrifugation. Lanes C and D show the insoluble and soluble proteins, respectively, present after removal of urea by dialysis. This indicates that human gastric lipase constitutes the major protein present in the soluble extract.

Employing broadly similar techniques, expression of genes coding for a human pregastric lipase or for a fusion protein including gastric lipase may be achieved. See for example the disclosures of published European patent application EP-A1-131363 for a description of the preparation of vectors capable of expressing a DNA sequence coding for chloroamphenicol acetyl transferase fusion proteins.

(ii) Expression of human gastric lipase in yeast

Figure 8:
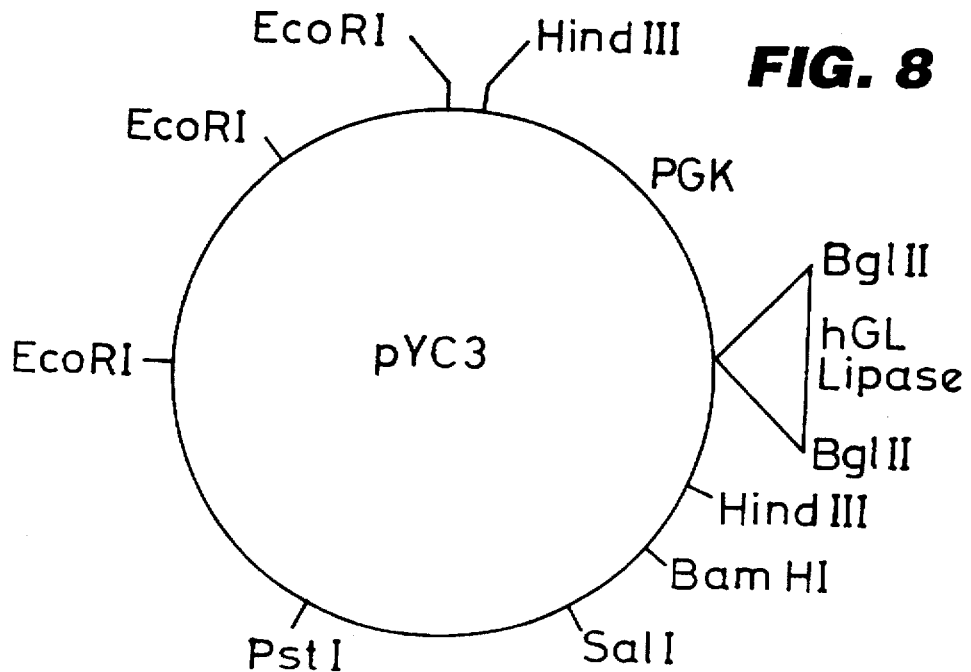
FIG. 8 shows a restriction endonuclease map of yeast plasmid pYC3.

Plasmid vectors for the expression of methionine human gastric lipase were constructed based on plasmid pMA91 (also known by the designation pMA3013) as described in the published european patent application EP-A2-0073653 (EP-A2-0073653 corresponds to U.S. Pat. No. 5,615,974, the contents of which are incorporated herein by reference). These vectors contain the yeast phosphoglycerate kinase (PGK) promoter and the PGK gene 3' and flanking sequences sandwiching the methionine-human gastric lipase DNA sequence. A plasmid pMB1 (not shown) was constructed by insertion of a BglII fragment containing the entire pre human gastric lipase DNA sequence. The plasmid pYC3 (FIG. 8) was constructed by removal of BglII to AccI fragment from pMB1 containing the 3' end of the lipase DNA sequence and ligated to the BglII to AccI fragment of the 5' end of the gene obtained from pCML1 (described above). This was inserted into the BglII site of pMA3013 to form pYC3. the plasmid pYC3 was transformed into the diploid strain MD50 and the haploid MD40/4C and transformants grown up in nitrogen based medium as described in the published European patent application EP-A2-0073653. Harvested cells were stored at −20° C.

A frozen slurry of yeast cells MD50 containing pYC3 was resuspended in 50 mM Tris pH7.5, 1 mM EDTA. All operations were carried out at 4° C. Cells were broken in a French Press by three passes at a pressure of 1,500 psi. Residual intact cells were removed by centrifugation at 800 g for 5 minutes. The supernatant, termed "total extract", was centrifuged at 20,000 g for 5 minutes to remove cell debris. The clear supernatant, termed "soluble extract" was retained for protein analysis by SDS-PAGE. The pelleted cell debris were washed in the above buffer by resuspension and recentrifugation. Washed cell debris were resuspended in an equal volume of the above buffer and samples were taken for SDS-PAGE. The above procedures were repeated on yeast MD40/4C cells bearing plasmid pYC3 and, as a control, yeast MD50 containing an equivalent plasmid to pYC3 but without the human gastric lipase DNA sequence. SDS-PAGE analysis of total protein extracts from these cells is seen in FIG. 9. Proteins were visualised by Coomassie blue staining. An arrow indicates the position of migration of recombinant human gastric lipase. Lanes A and B show the washed cell debris and soluble extract fractions respectively from yeast MD40/4C containing the control plasmid. No protein corresponding to human gastric lipase is visible. Lanes C and D represents, the debris and soluble extract fractions respectively from yeast MD/40 containing pYC3. Similarly, lanes E and F contain equivalent fractions from yeast MD50. A prominent protein is seen in the debris fraction of both yeast MD40/4C and MD50 containing pYC3 migrating in the expected position for recombinant human gastric lipase. Quantification of this protein by gel scanning indicated an expression level of 1%–3% of total protein (depending on fermentation batch).

A Western blot analysis was carried out on proteins present in yeast MD50/pYC3 (FIG. 10). The arrow labelled X (Lane A) indicates the position of migration of natural human gastric lipase. The arrow labelled Y indicates the position of the protein produced in DM50/pYC3, also indicated by an arrow in FIG. 10. Lanes B, C and D represent, respectively, an analysis of: total proteins; soluble extract and the cell debris fraction. A prominent band of human gastric lipase is seen migrating with an apparent molecular weight of approximately 40,000 in the total extract and insoluble debris fraction. Virtually no human gastric lipase was detectable in the soluble extract fraction. Lanes E, F and G represent analysis of the total proteins, soluble extract and debris fraction of yeast MD50 containing an equivalent plasmid of pYC3 but without the human gastric lipase gene. No human gastric lipase was detectable in these control cells. This analysis confirmed that yeast MD50/pYC3 expressed human gastric lipase. The Western blot analysis was repeated on yeast MD40/4C containing pYC3 with similar results. Again, a discrepancy is seen between the apparent molecular weights of natural human gastric lipase (approx. 50,000) and recombinant human gastric lipase (approx. 40,000). This may be due to an inability of yeast to carry out glycosylation of human gastric lipase produced intracellularly in yeast. The presence of lipolytically active human gastric lipase in yeast was shown by assay of total cell extracts and the soluble and insoluble fractions in the human gastric lipase activity assay. Soluble and insoluble extracts of MD50/pYC3, MD40(4C) pYC3 and MD50 control were made as described above with a "citrate-phosphate" buffer (50 mM sodium phosphate brought to pH5.4 with 50 mM citric acid) substituted for 0.05M Tris, 1 mM EDTA. 25 µl samples were taken from assay, as described above, using a triolein substrate at 37° C. The activity of recombinant human gastric lipase was compared with natural human gastric lipase as shown in Table II. Lipolytic activity was detected in the total extract and soluble and insoluble fractions. This activity was not present in control cells lacking the DNA sequence encoding human gastric lipase. From the lipase activity present in the total homogenate and an human gastric lipase expression level of approximately 3% total protein it can be calculated that approximately 5% and 18% of human gastric lipase produced in yeast MD40/4C and MD50 respectively was catalytically active.

TABLE II

Lipolytic Activity of human gastric lipase Expressed in Yeast

| Yeast Strain/Plasmid | Total extract | Activity* Soluble Fraction | Insoluble Fraction |
|---|---|---|---|
| MD40/4C/pYC3 | 14,967 | 8,250 | 8,792 |
| MD50/pYC3 | 27,445 | 14,394 | 12,040 |
| Control, MD50 | 2,677 | 1,761 | 1,374 |
| Buffer Blank | 3,630 | — | — |

*cpm, production of $^{14}$oleic acid from $^{14}$C-triolein; reaction conditions as described in the text. 1 ug natural human gastric lipase was equivalent to 7,995 cpm in this assay.

Employing broadly similar techniques expression of DNA sequences coding for human pregastric lipase or for a fusion protein including gastric lipase may be achieved.

(iii) Tissue Cultured Animal Cells

Plasmid vectors for the expression of human pregastric lipase are constructed based on vectors described by Pavlakis, G. N. and Hamer, D. H. (1983) Proc. Nat. Aca. Sci. USA 80, 397–401). These vectors contain metallothionine gene promoters and express prehuman gastric lipase. The enzyme produced in this system is secreted through the cellular membrane and is assayed in, and purified from the tissue culture medium as described above. The tissue cultured animal cells may possess the processing functions necessary to produce mature gastric lipase.

It will of course be understood that the present invention has been described above purely by way of example and modifications of detail can be made within the scope of the invention.

I claim:

1. A process for producing a methionine-gastric lipase protein from human gastric mucosal tissue comprising the steps:

providing an expression vector comprising a DNA sequence encoding a methionine-gastric lipase from human gastric mucosal tissue operably linked to transcriptional and translational control signals;

transforming a host cell with said expression vector;

culturing the transformed host under conditions such that the methionine-gastric lipase is produced; and isolating the methionine-gastric lipase produced.

2. A process for the production of a gastric lipase protein from human gastric mucosal tissue comprising the steps:

providing an expression vector comprising a DNA sequence encoding a gastric lipase precursor protein from human gastric mucosal tissue operably linked to transcriptional and translational control signals;

transforming a host cell with said expression vector;

culturing the transformed host under conditions such that the gastric lipase precursor protein is produced;

cleaving said gastric lipase precursor protein to produce gastric lipase protein; and isolating said gastric lipase protein.

3. The process according to claim 2, wherein the gastric lipase precursor protein is a pregastric lipase protein and the transformed host cell is capable of cleaving the pregastric lipase protein to produce a gastric lipase protein.

4. The process according to claim 3, wherein the host cell is a mammalian cell in tissue culture.

5. The process according to claim 2, wherein the gastric lipase precursor protein comprises a gastric lipase protein.

6. An isolated DNA encoding a protein comprising the amino acid sequence of a gastric lipase protein from human gastric mucosal tissue.

7. The DNA according to claim 6 encoding a methionine-gastric lipase protein.

8. The DNA according to claim 6 encoding a gastric lipase precursor protein.

9. The DNA according to claim 6 encoding a gastric lipase protein from human gastric mucosal tissue.

10. A vector comprising a DNA according to claim 6.

11. A host cell transformed with a vector according to claim 10.

12. The DNA according to claim 6, said DNA having the sequence:

AGAGAAACAGAATCCTAACTATTTCTGAGGAAACTGCAGGTCCAAAATGTGGCTGC

TTTTAACAATGGCAAGTTTGATATCTGTACTGGGGACTACACATGGTTTGTTTGGA

AAATTACATCCTGGAAGCCCTGAAGTGACTATGAACATTAGTCAGATGATTACTTA

-continued

```
TTGGGGATACCCAAATGAAGAATATGAAGTTGTGACTGAAGATGGTTATATTCTTG
AAGTCAATAGAATTCCTTATGGGAAGAAAAATTCAGGGAATACAGGCCAGAGACCT
GTTGTGTTTTTGCAGCATGGTTTGCTTGCATCAGCCACAAACTGGATTTCCAACCT
GCCGAACAACAGCCTTGCCTTCATTCTGGCAGATGCTGGTTATGATGTGTGGCTGG
GCAACAGCAGAGGAAACACCTGGGCCAGAAGAAACTTGTACTATTCACCAGATTCA
GTTGAATTCTGGGCTTTCAGCTTTGATGAAATGGCTAAATATGACCTTCCAGCCAC
AATCGACTTCATTGTAAAGAAAACTGGACAGAAGCAGCTACACTATGTTGGCCATT
CCCAGGGCACCACCATTGGTTTTATTGCCTTTTCCACCAATCCCAGCCTGGCTAAA
AGAATCAAAACCTTCTATGCTCTAGCTCCTGTTGCCACTGTGAAGTATACAAAAAG
CCTTATAAACAAACTTAGATTTGTTCCTCAATCCCTCTTCAAGTTTATATTTGGTG
ACAAAATATTCTACCCACACAACTTCTTTGATCAATTTCTTGCTACTGAAGTGTGC
TCCCGTGAGATGCTGAATCTCCTTTGCAGCAATGCCTTATTTATAATTTGTGGATT
TGACAGTAAGAACTTTAACACGAGTCGCTTGGATGTGTATCTATCACATAATCCAG
CAGGAACTTCTGTTCAAAACATGTTCCATTGGACCCAGGCTGTTAAGTCTGGGAAA
TTCCAAGCTTATGACTGGGGAAGCCCAGTTCAGAATAGGATGCACTATGATCAGTC
CCAACCTCCCTACTACAATGTGACAGCCATGAATGTACCAATTGCAGTGTGGAACG
GTGGCAAGGACCTGTTGGCTGACCCCCAAGATGTTGGCCTTTTGCTTCCAAAACTC
CCCAATCTTATTTACCACAAGGAGATTCCTTTTTACAATCACTTGGACTTTATCTG
GGCAATGGATGCCCCTCAAGAAGTTTACAATGACATTGTTTCTATGATATCAGAAG
ATAAAAAGTAGTTCTGGATTTAAAGAATTATCCGTTTGTTTTTCCAAAATACTTTA
TTCTCTCATACATAGTATTTTCATAATGTTTGACATGCAGTGCTTCTTTCTGTAAT
TTTGACTTTAGAAATATATTGGC.
```

13. The DNA according to claim 6, said DNA having the sequence:

```
TTGTTTGGAAAATTACATCCTGGAAGCCCTGAAGTGACTATGAACATTAGTCAGAT
GATTACTTATTGGGGATACCCAAATGAAGAATATGAAGTTGTGACTGAAGATGGTT
ATATTCTTGAAGTCAATAGAATTCCTTATGGGAAGAAAAATTCAGGGAATACAGGC
CAGAGACCTGTTGTGTTTTTGCAGCATGGTTTGCTTGCATCAGCCACAAACTGGAT
TTCCAACCTGCCGAACAACAGCCTTGCCTTCATTCTGGCAGATGCTGGTTATGATG
TGTGGCTGGGCAACAGCAGAGGAAACACCTGGGCCAGAAGAAACTTGTACTATTCA
CCAGATTCAGTTGAATTCTGGGCTTTCAGCTTTGATGAAATGGCTAAATATGACCT
TCCAGCCACAATCGACTTCATTGTAAAGAAAACTGGACAGAAGCAGCTACACTATG
TTGGCCATTCCCAGGGCACCACCATTGGTTTTATTGCCTTTTCCACCAATCCCAGC
CTGGCTAAAAGAATCAAAACCTTCTATGCTCTAGCTCCTGTTGCCACTGTGAAGTA
TACAAAAAGCCTTATAAACAAACTTAGATTTGTTCCTCAATCCCTCTTCAAGTTTA
TATTTGGTGACAAAATATTCTACCCACACAACTTCTTTGATCAATTTCTTGCTACT
GAAGTGTGCTCCCGTGAGATGCTGAATCTCCTTTGCAGCAATGCCTTATTTATAAT
TTGTGGATTTGACAGTAAGAACTTTAACACGAGTCGCTTGGATGTGTATCTATCAC
ATAATCCAGCAGGAACTTCTGTTCAAAACATGTTCCATTGGACCCAGGCTGTTAAG
```

-continued

TCTGGGAAATTCCAAGCTTATGACTGGGGAAGCCCAGTTCAGAATAGGATGCACTA

TGATCAGTCCCAACCTCCCTACTACAATGTGACAGCCATGAATGTACCAATTGCAG

TGTGGAACGGTGGCAAGGACCTGTTGGCTGACCCCCAAGATGTTGGCCTTTTGCTT

CCAAAACTCCCCAATCTTATTTACCACAAGGAGATTCCTTTTTACAATCACTTGGA

CTTTATCTGGGCAATGGATGCCCCTCAAGAAGTTTACAATGACATTGTTTCTATGA

TATCAGAAGATAAAAAG.

14. The DNA according to claim 7, said DNA having the sequence:

ATGTTGTTTGGAAAATTACATCCTGGAAGCCCTGAAGTGACTATGAACATTAGTCA

GATGATTACTTATTGGGGATACCCAAATGAAGAATATGAAGTTGTGACTGAAGATG

GTTATATTCTTGAAGTCAATAGAATTCCTTATGGGAAGAAAAATTCAGGGAATACA

GGCCAGAGACCTGTTGTGTTTTTGCAGCATGGTTTGCTTGCATCAGCCACAAACTG

GATTTCCAACCTGCCGAACAACAGCCTTGCCTTCATTCTGGCAGATGCTGGTTATG

ATGTGTGGCTGGGCAACAGCAGAGGAAACACCTGGGCCAGAAGAAACTTGTACTAT

TCACCAGATTCAGTTGAATTCTGGGCTTTCAGCTTTGATGAAATGGCTAAATATGA

CCTTCCAGCCACAATCGACTTCATTGTAAAGAAAACTGGACAGAAGCAGCTACACT

ATGTTGGCCATTCCCAGGGCACCACCATTGGTTTTATTGCCTTTTCCACCAATCCC

AGCCTGGCTAAAAGAATCAAAACCTTCTATGCTCTAGCTCCTGTTGCCACTGTGAA

GTATACAAAAAGCCTTATAAACAAACTTAGATTTGTTCCTCAATCCCTCTTCAAGT

TTATATTTGGTGACAAAATATTCTACCCACACAACTTCTTTGATCAATTTCTTGCT

ACTGAAGTGTGCTCCCGTGAGATGCTGAATCTCCTTTGCAGCAATGCCTTATTTAT

AATTTGTGGATTTGACAGTAAGAACTTTAACACGAGTCGCTTGGATGTGTATCTAT

CACATAATCCAGCAGGAACTTCTGTTCAAAACATGTTCCATTGGACCCAGGCTGTT

AAGTCTGGGAAATTCCAAGCTTATGACTGGGGAAGCCCAGTTCAGAATAGGATGCA

CTATGATCAGTCCCAACCTCCCTACTACAATGTGACAGCCATGAATGTACCAATTG

CAGTGTGGAACGGTGGCAAGGACCTGTTGGCTGACCCCCAAGATGTTGGCCTTTTG

CTTCCAAAACTCCCCAATCTTATTTACCACAAGGAGATTCCTTTTTACAATCACTT

GGACTTTATCTGGGCAATGGATGCCCCTCAAGAAGTTTACAATGACATTGTTTCTA

TGATATCAGAAGATAAAAAG.

15. The DNA according to claim 8, said DNA having the sequence:

ATGTGGCTGCTTTTAACAATGGCAAGTTTGATATCTGTACTGGGGACTACACATGG

TTTGTTTGGAAAATTACATCCTGGAAGCCCTGAAGTGACTATGAACATTAGTCAGA

TGATTACTTATTGGGGATACCCAAATGAAGAATATGAAGTTGTGACTGAAGATGGT

TATATTCTTGAAGTCAATAGAATTCCTTATGGGAAGAAAAATTCAGGGAATACAGG

CCAGAGACCTGTTGTGTTTTTGCAGCATGGTTTGCTTGCATCAGCCACAAACTGGA

TTTCCAACCTGCCGAACAACAGCCTTGCCTTCATTCTGGCAGATGCTGGTTATGAT

GTGTGGCTGGGCAACAGCAGAGGAAACACCTGGGCCAGAAGAAACTTGTACTATTC

ACCAGATTCAGTTGAATTCTGGGCTTTCAGCTTTGATGAAATGGCTAAATATGACC

-continued

TTCCAGCCACAATCGACTTCATTGTAAAGAAAACTGGACAGAAGCAGCTACACTAT

GTTGGCCATTCCCAGGGCACCACCATTGGTTTTATTGCCTTTTCCACCAATCCCAG

CCTGGCTAAAAGAATCAAAACCTTCTATGCTCTAGCTCCTGTTGCCACTGTGAAGT

ATACAAAAGCCTTATAAACAAACTTAGATTTGTTCCTCAATCCCTCTTCAAGTTT

ATATTTGGTGACAAAATATTCTACCCACACAACTTCTTTGATCAATTTCTTGCTAC

TGAAGTGTGCTCCCGTGAGATGCTGAATCTCCTTTGCAGCAATGCCTTATTTATAA

TTTGTGGATTTGACAGTAAGAACTTTAACACGAGTCGCTTGGATGTGTATCTATCA

CATAATCCAGCAGGAACTTCTGTTCAAAACATGTTCCATTGGACCCAGGCTGTTAA

GTCTGGGAAATTCCAAGCTTATGACTGGGGAAGCCCAGTTCAGAATAGGATGCACT

ATGATCAGTCCCAACCTCCCTACTACAATGTGACAGCCATGAATGTACCAATTGCA

GTGTGGAACGGTGGCAAGGACCTGTTGGCTGACCCCCAAGATGTTGGCCTTTTGCT

TCCAAAACTCCCCAATCTTATTTACCACAAGGAGATTCCTTTTTACAATCACTTGG

ACTTTATCTGGGCAATGGATGCCCCTCAAGAAGTTTACAATGACATTGTTTCTATG

ATATCAGAAGATAAAAAG.

16. The DNA according to claim 6, said DNA encoding a gastric lipase protein of the sequence:

Leu—Phe—Gly—Lys—Leu—His—Pro—Gly—Ser—Pro—Glu—Val—Thr—Met—
Asn—Ile—Ser—Gln—Met—Ile—Thr—Tyr—Trp—Gly—Tyr—Pro—Asn—Glu—
Glu—Tyr—Glu—Val—Val—Thr—Glu—Asp—Gly—Tyr—Ile—Leu—Glu—Val—
Asn—Arg—Ile—Pro—Tyr—Gly—Lys—Lys—Asn—Ser—Gly—Asn—Thr—Gly—
Gln—Arg—Pro—Val—Val—Phe—Leu—Gln—His—Gly—Leu—Leu—Ala—Ser—
Ala—Thr—Trp—Trp—Ile—Ser—Asn—Leu—Pro—Asn—Asn—Ser—Leu—Ala—
Phe—Ile—Leu—Ala—Asp—Ala—Gly—Tyr—Asp—Val—Trp—Leu—Gly—Asn—
Ser—Arg—Gly—Asn—Thr—Trp—Ala—Arg—Arg—Asn—Leu—Tyr—Tyr—Ser—
Pro—Asp—Ser—Val—Glu—Phe—Trp—Ala—Phe—Ser—Phe—Asp—Glu—Met—
Ala—Lys—Tyr—Asp—Leu—Pro—Ala—Thr—Ile—Asp—Phe—Ile—Val—Lys—
Lys—Thr—Gly—Gln—Lys—Gln—Leu—His—Tyr—Val—Gly—His—Ser—Gln—
Gly—Thr—Thr—Ile—Gly—Phe—Ile—Ala—Phe—Ser—Thr—Asn—Pro—Ser—
Leu—Ala—Lys—Arg—Ile—Lys—Thr—Phe—Tyr—Ala—Leu—Ala—Pro—Val—
Ala—Thr—Val—Lys—Tyr—Thr—Lys—Ser—Leu—Ile—His—Lys—Leu—Arg—
Phe—Val—Pro—Gln—Ser—Leu—Phe—Lys—Phe—Ile—Phe—Gly—Asp—Lys—
Ile—Phe—Tyr—Pro—His—Asn—Phe—Phe—Asp—Gln—Phe—Leu—Ala—Thr—
Glu—Val—Cys—Ser—Arg—Glu—Met—Leu—Asn—Leu—Leu—Cys—Ser—Asn—
Ala—Leu—Phe—Ile—Ile—Cys—Gly—Phe—Asp—Ser—Lys—Asn—Phe—Asn—
Thr—Ser—Arg—Leu—Asp—Val—Tyr—Leu—Ser—His—Asn—Pro—Ala—Gly—
Thr—Ser—Val—Gln—Asn—Met—Phe—His—Trp—Thr—Gln—Ala—Val—Lys—
Ser—Gly—Lys—Phe—Gln—Ala—Tyr—Asp—Trp—Gly—Ser—Pro—Val—Gln—
Asn—Arg—Met—His—Tyr—Asp—Gln—Ser—Gln—Pro—Pro—Tyr—Tyr—Asn—
Val—Thr—Ala—Met—Asn—Val—Pro—Ile—Ala—Val—Trp—Asn—Gly—Gly—
Lys—Asp—Leu—Leu—Ala—Asp—Pro—Gln—Asp—Val—Gly—Leu—Leu—Leu—
Pro—Lys—Leu—Pro—Asn—Leu—Ile—Tyr—His—Lys—Glu—Ile—Pro—Phe—
Tyr—Asn—His—Leu—Asp—Phe—Ile—Trp—Ala—Met—Asp—Ala—Pro—Gln—
Glu—Val—Tyr—Asn—Asp—Ile—Val—Ser—Met—Ile—Ser—Glu—Asp—Lys—
Lys.

17. The DNA according to claim 7, said DNA encoding a methionine-gastric lipase protein of the sequence:

Met—Leu—Phe—Gly—Lys—Leu—His—Pro—Gly—Ser—Pro—Glu—Val—Thr—
Met—Asn—Ile—Ser—Gln—Met—Ile—Thr—Tyr—Trp—Gly—Tyr—Pro—Asn—
Glu—Glu—Tyr—Glu—Val—Val—Thr—Glu—Asp—Gly—Tyr—Ile—Leu—Glu—
Val—Asn—Arg—Ile—Pro—Tyr—Gly—Lys—Lys—Asn—Ser—Gly—Asn—Thr—
Gly—Gln—Arg—Pro—Val—Val—Phe—Leu—Gln—His—Gly—Leu—Leu—Ala—
Ser—Ala—Thr—Trp—Trp—Ile—Ser—Asn—Leu—Pro—Asn—Asn—Ser—Leu—
Ala—Phe—Ile—Leu—Ala—Asp—Ala—Gly—Tyr—Asp—Val—Trp—Leu—Gly—
Asn—Ser—Arg—Gly—Asn—Thr—Trp—Ala—Arg—Arg—Asn—Leu—Tyr—Tyr—
Ser—Pro—Asp—Ser—Val—Glu—Phe—Trp—Ala—Phe—Ser—Phe—Asp—Glu—
Met—Ala—Lys—Tyr—Asp—Leu—Pro—Ala—Thr—Ile—Asp—Phe—Ile—Val—
Lys—Lys—Thr—Gly—Gln—Lys—Gln—Leu—His—Tyr—Val—Gly—His—Ser—
Gln—Gly—Thr—Thr—Ile—Gly—Phe—Ile—Ala—Phe—Ser—Thr—Asn—Pro—
Ser—Leu—Ala—Lys—Arg—Ile—Lys—Thr—Phe—Tyr—Ala—Leu—Ala—Pro—

-continued

Val—Ala—Thr—Val—Lys—Tyr—Thr—Lys—Ser—Leu—Ile—His—Lys—Leu—
Arg—Phe—Val—Pro—Gln—Ser—Leu—Phe—Lys—Phe—Ile—Phe—Gly—Asp—
Lys—Ile—Phe—Tyr—Pro—His—Asn—Phe—Phe—Asp—Gln—Phe—Leu—Ala—
Thr—Glu—Val—Cys—Ser—Arg—Glu—Met—Leu—Asn—Leu—Leu—Cys—Ser—
Asn—Ala—Leu—Phe—Ile—Ile—Cys—Gly—Phe—Asp—Ser—Lys—Asn—Phe—
Asn—Thr—Ser—Arg—Leu—Asp—Val—Tyr—Leu—Ser—His—Asn—Pro—Ala—
Gly—Thr—Ser—Val—Gln—Asn—Met—Phe—His—Trp—Thr—Gln—Ala—Val—
Lys—Ser—Gly—Lys—Phe—Gln—Ala—Tyr—Asp—Trp—Gly—Ser—Pro—Val—
Gln—Asn—Arg—Met—His—Tyr—Asp—Gln—Ser—Gln—Pro—Pro—Tyr—Tyr—
Asn—Val—Thr—Ala—Met—Asn—Val—Pro—Ile—Ala—Val—Trp—Asn—Gly—
Gly—Lys—Asp—Leu—Leu—Ala—Asp—Pro—Gln—Asp—Val—Gly—Leu—Leu—
Leu—Pro—Lys—Leu—Pro—Asn—Leu—Ile—Tyr—His—Lys—Glu—Ile—Pro—
Phe—Tyr—Asn—His—Leu—Asp—Phe—Ile—Trp—Ala—Met—Asp—Ala—Pro—
Gln—Glu—Val—Tyr—Asn—Asp—Ile—Val—Ser—Met—Ile—Ser—Glu—Asp—
Lys—Lys.

18. The DNA according to claim 8, said DNA encoding a pregastric lipase protein of the sequence:

Met—Trp—Leu—Leu—Leu—Thr—Met—Ala—Ser—Leu—Ile—Ser—Val—Leu—
Gly—Thr—Thr—His—Gly—Leu—Phe—Gly—Lys—Leu—His—Pro—Gly—Ser—
Pro—Glu—Val—Thr—Met—Asn—Ile—Ser—Gln—Met—Ile—Thr—Tyr—Trp—
Gly—Tyr—Pro—Asn—Glu—Glu—Tyr—Glu—Val—Val—Thr—Glu—Asp—Gly—
Tyr—Ile—Leu—Glu—Val—Asn—Arg—Ile—Pro—Tyr—Gly—Lys—Lys—Asn—
Ser—Gly—Asn—Thr—Gly—Gln—Arg—Pro—Val—Val—Phe—Leu—Gln—His—
Gly—Leu—Leu—Ala—Ser—Ala—Thr—Trp—Trp—Ile—Ser—Asn—Leu—Pro—
Asn—Asn—Ser—Leu—Ala—Phe—Ile—Leu—Ala—Asp—Ala—Gly—Trp—Asp—
Val—Trp—Leu—Gly—Asn—Ser—Arg—Gly—Asn—Thr—Trp—Ala—Arg—Arg—
Asn—Leu—Tyr—Tyr—Ser—Pro—Asp—Ser—Val—Glu—Phe—Trp—Ala—Phe—
Ser—Phe—Asp—Glu—Met—Ala—Lys—Tyr—Asp—Leu—Pro—Ala—Thr—Ile—
Asp—Phe—Ile—Val—Lys—Lys—Thr—Gly—Gln—Lys—Gln—Leu—His—Tyr—
Val—Gly—His—Ser—Gln—Gly—Thr—Thr—Ile—Gly—Phe—Ile—Ala—Phe—
Ser—Thr—Asn—Pro—Ser—Leu—Ala—Lys—Arg—Ile—Lys—Thr—Phe—Tyr—
Ala—Leu—Ala—Pro—Val—Ala—Thr—Val—Lys—Tyr—Thr—Lys—Ser—Leu—
Ile—His—Lys—Leu—Arg—Phe—Val—Pro—Gln—Ser—Leu—Phe—Lys—Phe—
Ile—Phe—Gly—Asp—Lys—Ile—Phe—Tyr—Pro—His—Asn—Phe—Phe—Asp—
Gln—Phe—Leu—Ala—Thr—Glu—Val—Cys—Ser—Arg—Glu—Met—Leu—Asn—
Leu—Leu—Cys—Ser—Asn—Ala—Leu—Phe—Ile—Ile—Cys—Gly—Phe—Asp—
Ser—Lys—Asn—Phe—Asn—Thr—Ser—Arg—Leu—Asp—Val—Tyr—Leu—Ser—
His—Asn—Pro—Ala—Gly—Thr—Ser—Val—Gln—Asn—Met—Phe—His—Trp—
Thr—Gln—Ala—Val—Lys—Ser—Gly—Lys—Phe—Gln—Ala—Tyr—Asp—Trp—
Gly—Ser—Pro—Val—Gln—Asn—Arg—Met—His—Tyr—Asp—Gln—Ser—Gln—
Pro—Pro—Tyr—Tyr—Asn—Val—Thr—Ala—Met—Asn—Val—Pro—Ile—Ala—
Val—Trp—Asn—Gly—Gly—Lys—Asp—Leu—Leu—Ala—Asp—Pro—Gln—Asp—
Val—Gly—Leu—Leu—Leu—Pro—Lys—Leu—Pro—Asn—Leu—Ile—Tyr—His—
Lys—Glu—Ile—Pro—Phe—Tyr—Asn—His—Leu—Asp—Phe—Ile—Trp—Ala—
Met—Asp—Ala—Pro—Gln—Glu—Val—Tyr—Asn—Asp—Ile—Val—Ser—Met—
Ile—Ser—Glu—Asp—Lys—Lys.

19. The DNA according to claim 6, said DNA encoding a gastric lipase fusion protein comprising the sequence:

Leu—Phe—Gly—Lys—Leu—His—Pro—Gly—Ser—Pro—Glu—Val—Thr—Met—
Asn—Ile—Ser—Gln—Met—Ile—Thr—Tyr—Trp—Gly—Tyr—Pro—Asn—Glu—
Glu—Tyr—Glu—Val—Val—Thr—Glu—Asp—Gly—Tyr—Ile—Leu—Glu—Val—
Asn—Arg—Ile—Pro—Tyr—Gly—Lys—Lys—Asn—Ser—Gly—Asn—Thr—Gly—
Gln—Arg—Pro—Val—Val—Phe—Leu—Gln—His—Gly—Leu—Leu—Ala—Ser—
Ala—Thr—Trp—Trp—Ile—Ser—Asn—Leu—Pro—Asn—Asn—Ser—Leu—Ala—
Phe—Ile—Leu—Ala—Asp—Ala—Gly—Tyr—Asp—Val—Trp—Leu—Gly—Asn—
Ser—Arg—Gly—Asn—Thr—Trp—Ala—Arg—Arg—Asn—Leu—Tyr—Tyr—Ser—
Pro—Asp—Ser—Val—Glu—Phe—Trp—Ala—Phe—Ser—Phe—Asp—Glu—Met—
Ala—Lys—Tyr—Asp—Leu—Pro—Ala—Thr—Ile—Asp—Phe—Ile—Val—Lys—
Lys—Thr—Gly—Gln—Lys—Gln—Leu—His—Tyr—Val—Gly—His—Ser—Gln—
Gly—Thr—Thr—Ile—Gly—Phe—Ile—Ala—Phe—Ser—Thr—Asn—Pro—Ser—
Leu—Ala—Lys—Arg—Ile—Lys—Thr—Phe—Tyr—Ala—Leu—Ala—Pro—Val—
Ala—Thr—Val—Lys—Tyr—Thr—Lys—Ser—Leu—Ile—His—Lys—Leu—Arg—
Phe—Val—Pro—Gln—Ser—Leu—Phe—Lys—Phe—Ile—Phe—Gly—Asp—Lys—
Ile—Phe—Tyr—Pro—His—Asn—Phe—Phe—Asp—Gln—Phe—Leu—Ala—Thr—
Glu—Val—Cys—Ser—Arg—Glu—Met—Leu—Asn—Leu—Leu—Cys—Ser—Asn—
Ala—Leu—Phe—Ile—Ile—Cys—Gly—Phe—Asp—Ser—Lys—Asn—Phe—Asn—
Thr—Ser—Arg—Leu—Asp—Val—Tyr—Leu—Ser—His—Asn—Pro—Ala—Gly—
Thr—Ser—Val—Gln—Asn—Met—Phe—His—Trp—Thr—Gln—Ala—Val—Lys—
Ser—Gly—Lys—Phe—Gln—Ala—Tyr—Asp—Trp—Gly—Ser—Pro—Val—Gln—
Asn—Arg—Met—His—Tyr—Asp—Gln—Ser—Gln—Pro—Pro—Tyr—Tyr—Asn—
Val—Thr—Ala—Met—Asn—Val—Pro—Ile—Ala—Val—Trp—Asn—Gly—Gly—
Lys—Asp—Leu—Leu—Ala—Asp—Pro—Gln—Asp—Val—Gly—Leu—Leu—Leu—

-continued

Pro—Lys—Leu—Pro—Asn—Leu—Ile—Tyr—His—Lys—Glu—Ile—Pro—Phe—Tyr—Asn—His—Leu—Asp—Phe—Ile—Trp—Ala—Met—Asp—Ala—Pro—Gln—Glu—Val—Tyr—Asn—Asp—Ile—Val—Ser—Met—Ile—Ser—Glu—Asp—Lys—Lys.

20. Plasmid pGL17.

21. Plasmid pCML1.

22. Plasmid pMG197.

* * * * *